United States Patent [19]
Massague et al.

[11] Patent Number: 6,025,480
[45] Date of Patent: Feb. 15, 2000

[54] ISOLATED NUCLEIC ACID MOLECULES ENCODING P57KIP2

[75] Inventors: Joan Massague; Mong-Hong Lee, both of New York, N.Y.

[73] Assignee: Sloan-Kettering Institute for Cancer Research, New York, N.Y.

[21] Appl. No.: 08/415,655

[22] Filed: Apr. 3, 1995

[51] Int. Cl.[7] .......................... C07M 21/02; C02H 21/04; C12N 15/70; C12N 1/21

[52] U.S. Cl. .................... 536/23.1; 536/22.1; 536/24.31; 536/24.33; 435/24.02; 435/320.1

[58] Field of Search ................................. 536/22.1, 23.1, 536/24.3, 24.31, 24.33; 435/240.2, 320.1

[56] References Cited

U.S. PATENT DOCUMENTS

| | | | |
|---|---|---|---|
| 4,683,195 | 7/1987 | Mullis | 435/6 |
| 4,683,202 | 7/1987 | Mullis | 435/6 |
| 4,745,051 | 5/1988 | Smith et al. | 435/68 |
| 5,302,706 | 4/1994 | Smith | 536/23.1 |

OTHER PUBLICATIONS

Ausebel, F.M. et al., (1992) "Manipulation of Yeast Genes," *Short Protocols in Molecular Biology*, John Wiely & Sons, New York, 13–29 to 13–30 (Exhibit 5).

Auselbel, F.M., et al., (1995) *Current Protocols in Molecular Biology*, John Wiley & Sons, New York, 3.5.9–3.5.10 and 5.5.1–5.5.11 (Exhibit 6).

Bai, C. et al., (1994) "Human Cyclin F.," *EMBO J.*, 13:6087–6098 (Exhibit 7).

Boshart, M. et al., (1985) A Very Strong Enhancer is Located Upstream of an Immediate Early Gene of Human Cytomegalovirus, *Cell*, 41:521 (Exhibit 8).

Breeden, L. and Nasmyth, K., (1985) "Regulation of the Yeast HO Gene," *Cold Spring Harbor Symp. Quant. Biol.*, 50:643–650 (Exhibit 9).

Cairns, P. et al., (1994) "Rates of p16 [MTS1] Mutations in Primary Tumors with p9 Loss," *Science*, 265:415–417 (Exhibit 10).

Chamberlin, M. et al., (1970) "New RNA Polymerase from *Escherichia coli* Infected with Bacteriophage T7," *Nature*, 228:227–231 (Exhibit 11).

Dijkema, R. et al., 91985) "Cloning and Expression of the Chromosomal Immune Interferon Gene of the Rat," *EMBO J.*, 4:761 (Exhibit 12).

Draetta, G., (19930 "Cdc2 Activation: The Interplay of Cyclin Binding and Thr16l Phosphorylation," *Trends Cell Biol.*, 3:287–289 (Exhibit 13).

Dulic, V. et al., (1994) "p53–Dependent Inhibition of Cyclin Dependent Kinase Activities in Human Fibroblasts During Radiation–Induced GI Arrest," *Cell*, 76:1013–1023 (Exhibit 14).

Durfee, T. et al., (1993) "The Retinoblastoma Protein associates With the Protein Phosphatase Type I Catalytic Subunit," *Genes & Dev.*, 7:555–569 (Exhibit 15).

El–Diery, W.S., (1993) "WAF1, A Potential Mediator of p53 Tumor Suppression," *Cell*, 75:817–825 (Exhibit 16).

El–Diery, W.S., (1994) "WAF1/CIP1 is Induced in p53 Medicated $G_1$ Arrest and Apoptosis[1]," *Cancer Res.*, 54:1169–1174 (Exhibit 17).

Elledge, S.J. et al., (1992) "CDK2 Encodes a 33–kDa Cyclin A–Associated Protein Kinase and is Expressed Before CDC2 in the Cell Cycle," *Proc. Natl. Acad. Sci. USA*, 89:2907–2911 (Exhibit 18).

Erlich, H.A. (ed.), PCR Technology, (1989) "Taq DNA Polymerase," Stockton Press., 17–22 (Exhibit 20).

Florez–Rozas, H. et al., (1994) "Cdk–Interacting Protein–1 Directly Binds with Proliferating Cell Nuclear Antigen and Inhibits DNA Replication Catalyzed by the DNA Polymerase δ Holoenzyme," *Proc. Natl. Acad. Sci. USA*, 91:8655–8659 (Exhibit 21).

Gorman, C.M. et al., (1982) "The Rous Sarcoma Virus long Terminal Repeat is a Strong Promoter When Introduced into a Variety of Eukaryotic Cells by DNA–Mediated Transfection," *Proc. Natl. Acad. Sci. USA*, 79:6777 (Exhibit 22).

Graham and van der Eb, (1973) "A New Technique for the Assay of Infectivity of Human Adenovirus 5 DNA," *Virol.*, 52:456–467 (Exhibit 23).

Guan, K. et al., (1994) "Growht Suppression by p18, a $P16_{ink4b/MTS1}$ –and $ph14^{INK4B/MTS2}$–Related CDK6 Inhibitor, Correlates with Wild–Type pRb Function," *Genes and Dev.*, 8:2939–2952 (Exhibit 24).

Gubler, U. and Hoffman, B.J., (1983) "A Simple and Very Efficient Method for Generating cDNA libraries," *Gene*, 25:263–269 (Exhibit 25).

Halvey,O., et al. (1995) "Correlation Terminal Cell Cycle Arrest of Skeletal Muscle with Induction of P21 by MyoD," *Science*, 267:1018–1021 (Exhibit 26).

Hannon, G.J. and Beach, D., (1994) "$P15^{ink4b}$ is a Potential Effector of TGF–β Induced Cell Cycle Arrest," *Nature*, 371:257–261 (Exhibit 27).

Harlow, E. and Lane, E., (1988) *Antibodies: A Laboratory Manual* Cold Spring Harbor Press, New York, 117,119,498, 522:33 (Exhibit 28).

Harper et al., (1995) "Inhibition of Cyclin–dependent Kinases by p21," *Mol. Bio. Cell*, 6:387–400 (Exhibit 29).

(List continued on next page.)

*Primary Examiner*—Jeffrey Fredman
*Attorney, Agent, or Firm*—John P. White; Cooper & Dunham LLP

[57] ABSTRACT

This invention provides an isolated nucleic acid molecule encoding a mammalian $p57^{KIP2}$. This invention also provides vectors comprising the isolated nucleic acid molecule encoding a mammalian $p57^{KIP2}$. This invention further provides a host vector system for the production of a mammalian $p57^{KIP2}$. This invention also provides probes for the isolated nucleic acid molecule encoding a mammalian $p57^{KIP2}$. This invention provides antibodies directed against a mammalian $p57^{KIP2}$. This invention also provides transgenic animals comprising isolated nucleic acid molecules encoding a mammalian $p57^{KIP2}$. Finally, this invention provides different uses of the mammalian $p57^{KIP2}$.

18 Claims, 14 Drawing Sheets

OTHER PUBLICATIONS

Hastie, N.D., (1994) "The Genetics of Wilms Tumor–A Case of Disrupted Development," *Genetics,* 28:523–558 (Exhibit 30).

Hunter, T. and Pines, J., (1994) "Cyclins and Cancer II: Cyclin D and CDK Inhibitors Come of Age," *Cell,* 79:573–582 (Exhibit 31).

Ijdo, J.W. et al., (1992) "Multiple Variants in Subtelomeric Regions of Normal Karyotypes," *Genomics,* 14:1019–1025 (Exhibit 32).

Jen, J. et al., (1994) "Deletion of p16 and p15 Genes in Brian Tumors," *Cancer Res.,* 54:6353–6358 (Exhibit 33).

Jiang, H. et al., (1994) "Induction of Differentiationin Human Promyelocytic HL–60 Leukemia Cells Activates p21, WAFI/CIP1, Expression in the Absence of p53," *Oncogene,* 9:3389–3396 (Exhibit 34).

Junien, C., (1992) "Beckwith–Wiedemann Syndrom, Tumourigenesis and Imprinting," *Curr. Op. Genet. Dev.,* 2;431–438 (Exhibit 35).

Kacian, D.L. et al., (1972) "A Replicating RNA Molecule Suitable for a Detailed Analysis of Extracellular Evolution and Replication," *Proc. Natl. Acad. Sci. USA,* 69:3038–3042 (Exhibit 36).

Kato, J. et al., (1994) "Cyclic AMP–Induced GI Phase Arrest Mediated by an Inhibitor (p27$^{Kip1)}$ " *Cell,* 7:487–496 (Exhibit 37).

Kim, D.W. et al., (1990) "Use of the Human Elongation Factor 1α Promoter as a Versatile and Efficient Expression System," *Gene,* 91:217 (Exhibit 38).

Lutz, B. et al., (1994) "Development Regulation of the Orphan Receptor COUP–TF II Gene in Spinal Motor Neurons," *Development,* 120:25–36 (Exhibit 40).

Maniatis, T. et al., (1987) "Regulation of Inducible and Tissue–specific Gene Expression," *Science,* 236:1237 (Exhibit 41).

Martinez, J. et al., (1991) "Cellular Localization and Cell Cycle Regulation by a Temperature–Sensitive p53–Protein," *Genes & Dev.,* 5:151–159 (Exhibit 42).

Matsushime, H. et al., (1992) "Identification and Properties of an atypical Catalytic Subunit (p34$^{psk-J3}$/cdk4) for Mamalian D–type GI Cyclins," *Cell,* 71:323–334 (Exhibit 44).

Meyerson, M. and Harlow, E., (1994) "Identification of GI Kinase Activity for cdk6, A Novel Cyclin D Partner," *Mol. Cell. Biol.,* 14:2077–2086 (Exhibit 45).

Michieli, P. et al., (1994) "Induction of WAF1/CIP1 by a p53–Independent Pathway," *Cancer Res.,* 54:3391–3395 (Exhibit 46).

Mizushima, S. and Nagata, S. (1990) "Pef–BOS, A Powerful Mammalian Expression Vector," *Nuc. Acids. Res.,* 18:5322 (Exhibit 47).

Nasmyth, K. and Hunt, T., (1993) "Dams and Sluices," *Nature,* 366:634–635 (Exhibit 48).

Nohori, T.K. et al., (1994) "Deletions of the Cyclin–Dependent Kinase–4 Inhibitor Gene in Multiple Human Cancers," *Nature,* 368:753–756 (Exhibit 49).

Noda, A. et al., (1994) "Cloning of Senescent Cell–Derived Inhibitors of DNA Synthesis Using an Expression Cloning Screen," *Exp. Cell. Res.,* 211:90–98 (Exhibit 50).

Nourse, J. et al., (1994) "Interleukin–2–Mediated Elimination of the p27$^{Kip1}$ Cyclin–Dependent Kinase Inhibitor Prevented by Rapamycin," *Nature,* 372:570–573 (Exhibit 51).

Parker, S.B. et al., (1995) "p53–Independent Expression of p21$^{Cip1}$ in Muscle and Other Terminally Differentiating Cells," *Science,* 267:1024–1027 (Exhibit 52).

Pettenatti, M.J. et al., (1986) "Beckwith–Wiedenmann Syndrome: Presentation of Clinical and Cytogenetic Data on 22 New Cases and Review of the Literature," *Hum. Genet.,* 74:143–154 (Exhibit 53).

Pines, J., (1993) "Cyclins and Cyclin–Dependent Kinases: Take Your Partners," *TIBS,* 18:195–197 (Exhibit 54).

Sambrook, J. et al., (1989) *Molecular Cloning: A Laboratory Manual, 2$^{nd}$ ed.,* Cold Spring Harbor Laboratory Press, New York, 1.33–1.48, 2.67–2.81, 2.108–2.111, 7.6–7.11, 7.39–7.52, 9.31–9.58 and 16.6–16.15 (Exhibit 55).

Seizinger, B. et al., (1991) "Report of the Committee on Chromosome and Gene Loss in Human Neoplasia," *Cytogenet. Cell. Genet.,* 58:1080–1096 (Exhibit 56).

Serrano, M. et al., (1993) "A New Regulatory Motif in Cell–Cycle Control Causing Specific Inhibition of Cyclin D/CDK4," *Nature,* 366:704–707 (Exhibit 57).

Sheiki, M.S. et al., (1994) "Mechanisms of Regulation of WAF1/Cip1 Gene Expression in Human Breast Carcinoma: Role of p53–Dependent and Independent Signal Transduction Pathways," *Oncogene,* 9:3407–3415 (Exhibit 58).

Sherr, C.J., (1994) "GI Phase Progression: Cycling on Cue," *Cell,* 79:551–555 (Exhibit 59).

Spruck, C.H. et al., (1994) "p16 Gene in Uncultured Tumours," *Nature,* 370:183–184 (Exhibit 60).

Soloman, M.J., (1993) "Activation of the Various Cyclin/cdc2 Protein Kinases," *Curr. Opin. Cell Biol.* 5:180–186 (Exhibit 61).

Steinman, R.A. et al., (1994) "Induction of p21 (WAF–1/CIP1) during differentiation," *Oncogene,* 9:3389–3396 (Exhibit 62).

Sternberg, N., (1990) "Bacteriophage P1 Cloning System for the Isolation, Amplification, and Recovery of DNA Fragments as Large as 100 Kilobase Pairs," *Proc. Natl. Acad. Sci. USA,* 87:103–107 (Exhibit 63).

Sundin, O.H. et al., (1990) "Region–specific Expression in Early Chick and Mouse Embryos of Ghox–lab and Hox 1.6, Vertebrate Homeobox–Containing Genes Related to Drosophila Labial," *Development,* 108:47–58 (Exhibit 64).

Uetsuki, T. et al., (1989) "Isolation and Characterization of the Human Chromosomal Gene for Polypeptide Chain Elongation Factor–1α," *J.Biol. Chem.,* 264:5791 (Exhibit 65).

van der Heuvel, S. and Harlow, E., (1993) "Distinct Roles for Cyclin–Dependent Kinases in Cell Cycle Control," *Science,* 26:2050–2054 (Exhibit 66).

Voss, S.D. et al., (1986) "The Role of Enhancers in the Regulation of Cell–Type–Specific Transcriptional Control," *Trends Biochem. Sci.,* 11:287 (Exhibit 67).

Waga, S. et al., (1994) "The p21 Inhibitor of Cyclin–Dependent Kinases Controls DNA Replication by Interaction with PCNA," *Nature,* 369:574–578 (Exhibit 68).

Weidemann, H.R., (1983) "Tumours and Hemihypertrophy Associated with Wiedemann–Beckwith Syndrome," *Eur. J. Pediatr.,* 141:129 (Exhibit 69).

Wu, D.Y. and Wallace, R.B., (1989) "The Ligation Amplification Reaction(LAR)–Amplification of Specific DNA Sequences Using Sequential Rounds of Template–Dependent Ligation," *Genomics,* 4:560–569 (Exhibit 70).

Xiong, Y. et al., (1993) "p21 is a Universal Inhibitor of Cyclin Kinases," *Nature,* 366:701–704 (Exhibit 71).

Zhang, H. et al., (1994) "p–21–Containing Cyclin Kinases Exist in Both Acti ve and Inactive States," *Genes Dev.,* 8:1750–1758 (Exhibit 72); and.

Zhu, L. et al., (1993) "Inhibition of Cell Proliferation by p107, A Relative of the Retinoblastoma Protein," *Genes & Dev.,* 7:1111–1125 (Exhibit 73).

Alexandrow et al, (Apr. 1995), "Transforming growth factor β and cell cycle regulation" Cancer Res. 55:1452–1457.

Elledge et al, (1994), "Cdk inhibitors: on the threshold of checkpoints and development", Current Opin. Cell Biol. 6:847–852.

Harper, J. Wade et al., "The p21 Cdk–Interacting protein Cip1 is a Potent Inhibitor of G1 Cyclin–dependent Kinases." Cell (1993), 75:805–816 (Exhibit B).

Polyak Kornelia et al., "Cloning of p27$^{kip1}$, a Cyclin–Dependent Kinase Inhibitor and a Potential Mediator of Extracellular Antimitogenic Signals." Cell (1994), 78:59–66 (Exhibit C).

Polyak Kornelia et al., "P27$^{kip1}$, a Cyclin–Cdk Inhibitor, Links Transforming Growth Factor–β and Contact Inhibition to Cell Cycle Arrest." Genes & Development (1994), 8:9–22 (Exhibit D).

Toyoshima Hideo and Hunter Tony, "p27, a Novel Inhibitor of G1 yclin–Cdk protein Kinase Activity, is Related to p21." Cell (1994), 78:67–73 (Exhibit E).

Matsuoka et al, "P57kip2, a structurally distinct member of the p21cip1 cdk inhibitor family, is a candidate tumor suppressor gene", Genes Dev. 9:650–662, Mar. 15, 1995.

Lee et al, "Cloning of p57kip2, a cyclin dependent kinase inhibitor with unique domain structure and tissue distribution", Genes Dev. 9:639–649, Mar. 15, 1995.

FIGURE 1A

```
   1 cgcaggagc cgtccatcac caatcagcca gccttcgacc atgggcatgt ccgacgtgta
  61 cctccgcagc agaacagcga tggaacgctt ggcctccagc gataccttcc cagtgatagc
 121 gcgtagcagc gcctgccgca gcctcttcgg gcctgtagac cacgaggagc tgggccgcga
 181 gctgcggatg cgcctggccg agctgaacgc cgaggaccag aaccgctggg acttcaactt
 241 ccagcaggat gtgcctcttc gaggccctgg tcgtctgcag tggatggagg tggacagcga
 301 gtctgtgccc gcctctacc gcgagacggt gcaggtgggg cgctgtcgcc tgcagctggg
 361 gccccggcca ccccggtgg ccgtggctgt catcccgcgt tctgggccgc cggctggcga
 421 ggcccccgac ggcctagagg agcgcctga gcagccgccc agcgccccag cctcggccgt
 481 ggtcgcggac gccacccccac ccgcgacccc ggcccccgct tcagatctga cctcagaccc
 541 aattccggag gtgaccctgg tcgcgaccct cgaccccgact cgaccccga tccccgacgc
 601 gaacccggac gtggcgactc gggacggcga ggaacaggtc cctgagcagg tctctgagca
 661 gggcgaggag tcgggtgctg agccgggtga tgagctggga actgagccgg tctctgagca
 721 gggcgaggag cagggcgcag agccggtcga gccggtgga ggagaaggac gaggagccgg aggaggagca
 781 gggcgcggag ccggtcgagg agcaggggtgc ggagccggtc gaggagcaga atggggagcc
 841 ggtcgaggag caggacgaga atcaagagca gcgcggcag gagctgaagg accagcctct
 901 ctcggggatt ccaggacgtc ctgcaccggg gactgctgcg gccaatgcga acgacttctt
 961 cgccaagcgc aagagaaactg cgcaggagaa caagcgtcg aacgacgtcc ctccagggtg
1021 tccctctcca aacgtggctc ctggggtggg cgcggtggag cagacccgc gcaaacgtct
1081 gagatgagtt agtttagagg ctaacggcca gagagaactt gctgggcatc tgggcagcgg
1141 acgatggaag aactctgggc ttcgctgggg acctttcgtt catgtagcag gaaccggaga
1201 tggttgcgta gagcagccca cggtttgtg gaaatctgaa aactgtgcaa tgtattgaga
1261 acactctgta ccatgtgcaa ggagtacgct ggtccccagg tgtaaagctt taaatcattt
1321 atgtaaaatg tttaatctct actcgctctc agtgc
```

FIGURE 1B

```
CDS    41..1087
       /codon_start=1
       /function="cyclin-dependent kinase inhibitor"
       /product="p57kip2"
       /translation="MGMSDVYLRSRTAMERLASSDTFPVIARSSACRSLFGPVDHEEL
       GRELRMRLAELNAEDQNRWDFNFQQDVPLRGPGRLQWMEVDSESVPAFYRETVQVGRC
       RLQLGPRPPVAVAVIPRSGPPAGEAPDGLEEAPEQPPSAPASAVVADATPPATPAPA
       SDLTSDPIPEVTLVATSDPTPDPIPDANPDVATRDGEEQVPEQVSEQGEESGAEPGDE
       LGTEPVSEQGEEQGAEPVEEKDEEPEEEQGAEPVEEQGAEPVEEQNGEPVEEQDENQE
       QRGQELKDQPLSGIPGRPAPGTAAANANDFFAKRKRTAQENKASNDVPPGCPSPNVAP
       GVGAVEQTPRKRLR"
```

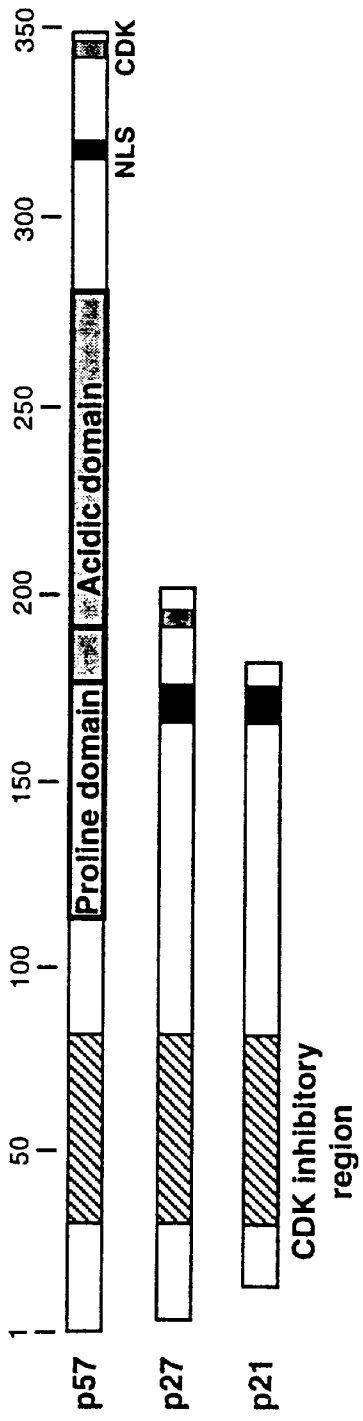

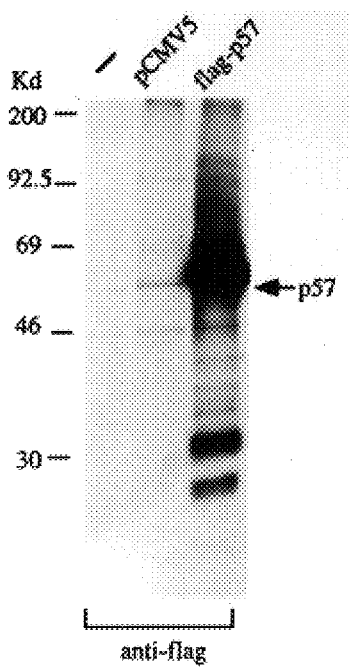
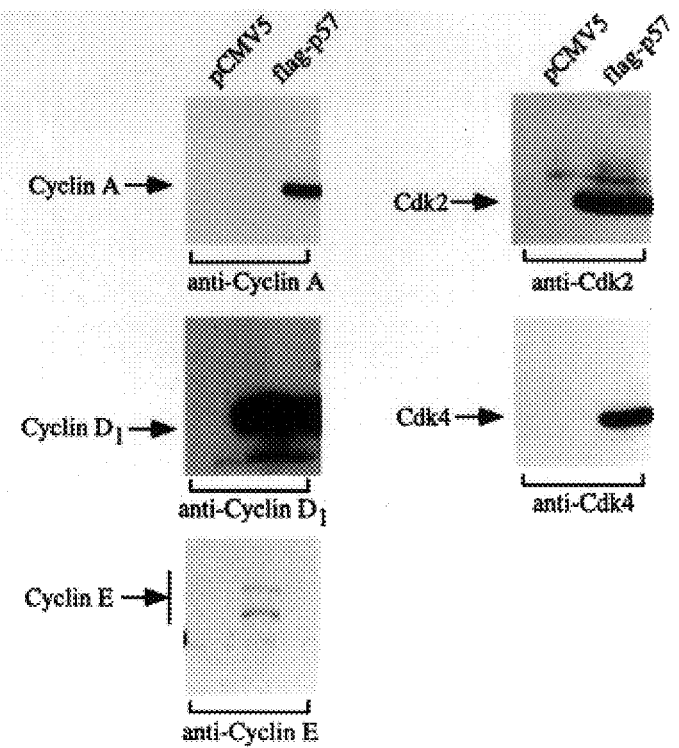
FIG. 6A
FIG. 6B

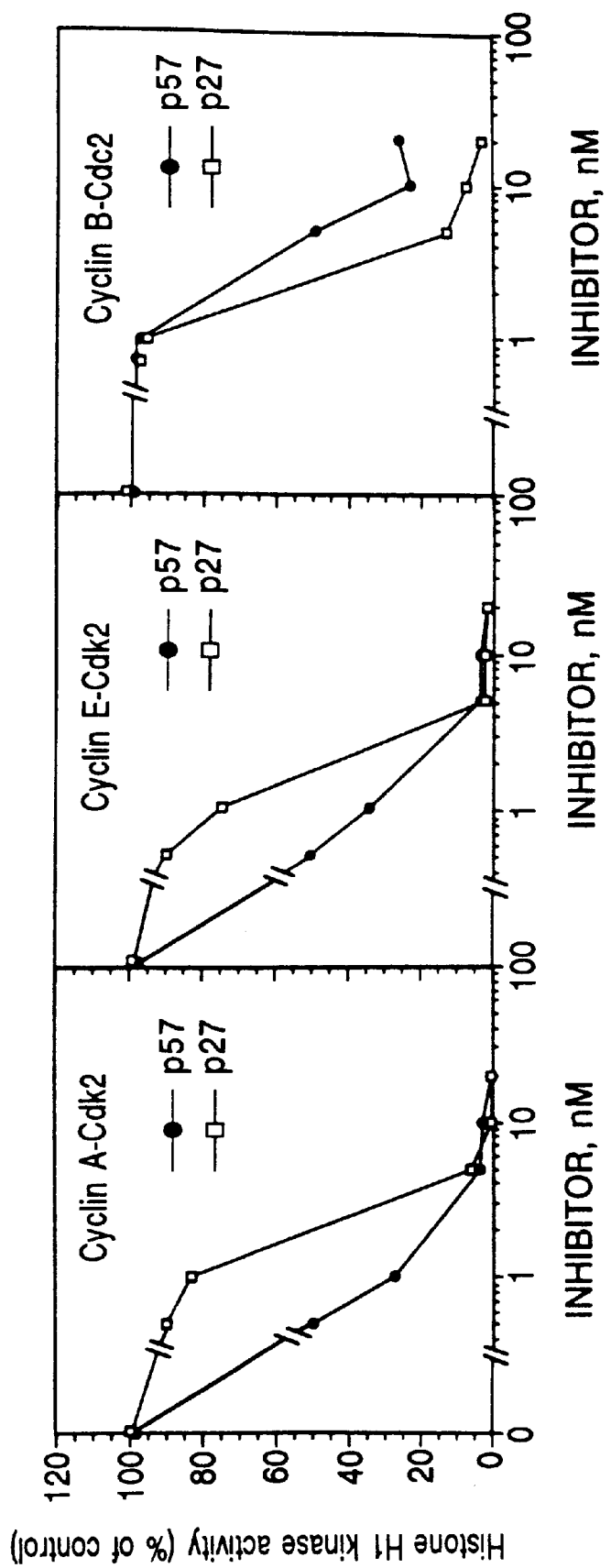

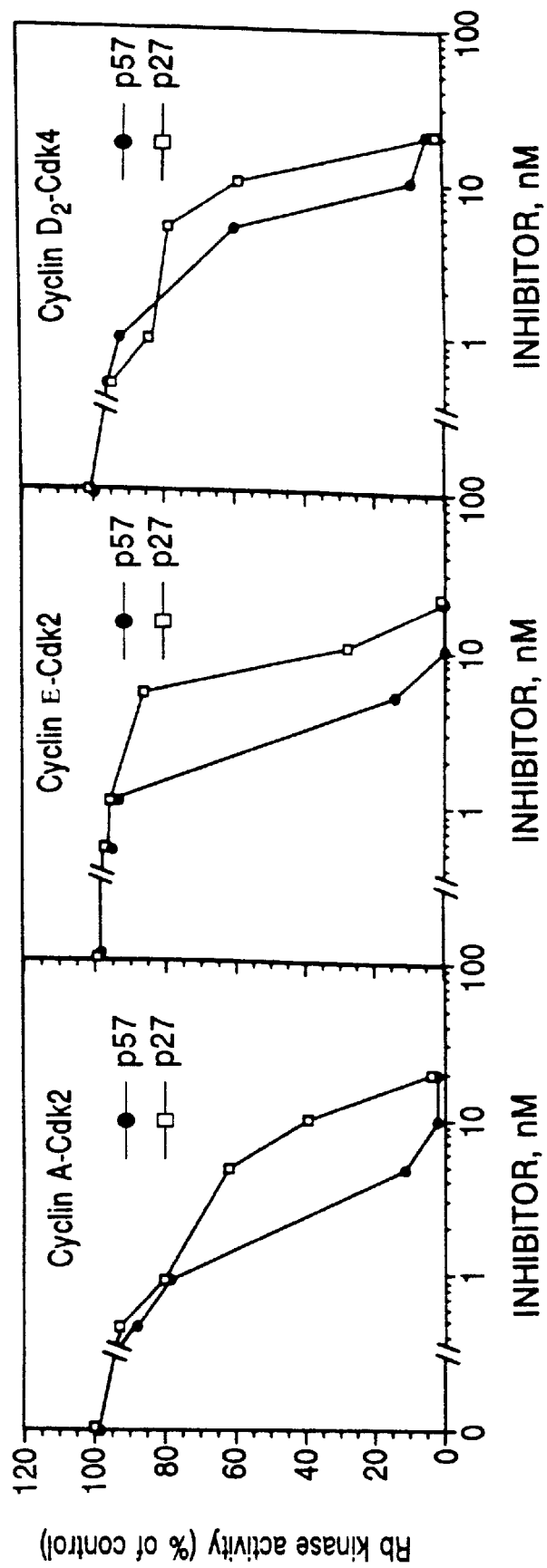

| Transfection | %G1 | %S | %G2/M | $^{125}$I-dU(cpm) |
|---|---|---|---|---|
| pCMV5 | 37.1 | 36.7 | 26.2 | 1,417±47 |
| p57$^{Kip2}$ | 88.7 | 6.4 | 4.9 | 442±21 |
| p27$^{Kip1}$ | 88.8 | 3.7 | 7.5 | 437±10 |

FIGURE 10

HUMAN p57 PARTIAL SEQUENCE

```
  1 CGAGCGTATC GATAAGCTTG ATATCGAATT CCGGTTTTTT CTTTTTTCTT TTTTTGCAC
 61 TGAGTTTCAG CAGAGATTAA ACATTTTATA TAAATGACTC TTAAAGCTTT ACACCTTGGG
121 ACCAGTGTAC CTTCTCGTGC AGAATACATT TAGATATAAA AAGACGTTAT TAATACATTG
181 CACAGTTTTC AAAATTTAAA ACAAAACCG AACGCTGCTC TGCGGCACGC GCCGGCGTTG
241 CTGCTACATG AACGGTCCCA GCCGAGGCCC AGCGCCCTTC CAACGTCCGC TGCCCCGGCA
301 GGTTCCCTCG GGGCTCTTTG GGCTCTAAAT TGGCTCACCG CAGCCTCTTG CGCGGGGTCT
361 GCTCCACCGA GCCCACGCCA GGGGCGGCGC TTGGAGAGGG ACACGGGCG GGGACATGC
421 CCGACGACTT CTCAGGCGCT GATCTCTTGC GCTTGGCGAA GAAATCGGAG ATCAGAGGCC
481 CGGACAGCTT CTTGATCGCC GCGCCGTTGG CGTGGCGGCC CCGGGCCGGT
541 CCCGAAATCC CCGAGTGCAG CTGGTCAGCG AGAGGCTCCT GGCCGCGCTG CCCCTGGTTC
601 GCGCCCTGCT CGGGCGCTC TTGAGGGCC GCGTCCGGGG CCGGGGCCGG GGGGGGGCC
661 GGGGCCGGGG CCGGGGCCGG GGCTGGGGCC CTGGAGCCGG GGCCGGAGCC
721 GGAGCCGGAG CCGGGGCCGG GCGGGCAGGA CCGGCGACGGA CCGAGCGCCGA CCGA
```

ISOLATED NUCLEIC ACID MOLECULES ENCODING P57KIP2

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Cell cycle progression is controlled by cyclin-dependent kinases (CDKs) counterbalanced by CDK inhibitors (CDIs) (reviewed in Hunter and Pines 1994; Sherr 1994a). During $G_1$ phase, these two activities respond in opposite ways to regulatory signals, and the outcome determines whether a cell will complete the division cycle. The best characterized CDKs that control mammalian $G_1$ progression include the catalytic subunit cdk2 associated with the activating subunit cyclin E and cdk4 or its isoform cdk6 associated with any one of three cyclin D isoforms. These complexes become activated upon phosphorylation of the cdk subunit by CAK (cdk activating kinase), itself a CDK-related kinase complex (Sherr 1994a). A prominent substrate for $G_1$ CDKs is the retinoblastoma protein Rb (reviewed in Hinds and Weinberg 1994; Sherr 1994b). Rb phosphorylation in mid $G_1$ phase liberates bound factors including E2F-DP1 heterodimers that are essential for DNA replication. Cdk4 is thought to catalyze a first wave of Rb phosphorylation whereas cdk2, which is active later in $G_1$, may help keep Rb and other substrates in the phosphorylated state. These events allow passage through the 'Restriction' or 'Start' checkpoint beyond which the cell cycle advances on its own, no longer influenced by external signals.

Although regulatory signals can control CDK activity by affecting the expression of CDK components (Cocks et al. 1992; Ewen et al. 1993; Geng and Weinberg 1993; Matsushime et al. 1991), a major venue for CDK regulation by these signals is through the CDIs. The mammalian CDIs described to date fall into two gene families. One family includes p16$^{INK4A}$ (Serrano et al. 1993), p15$^{INK4B}$ (Hannon and Beach 1994), p18 and related proteins of 15–20 kD (Guan et al. 1994; Hannon and Beach 1994), all containing a characteristic four-fold repeated ankyrin-like sequence. The INK4s are specific for cdk4 and cdk6, and appear to compete with cyclin D for binding to these kinases (Serrano et al. 1993). p16 is overexpressed in cells defective in Rb function (Li et al. 1994b; Serrano et al. 1993) and may participate in a feed-back loop wherein repression of p16 expression by Rb may allow cdk4 to phosphorylate and inhibit Rb. p15 is upregulated by the antimitogenic cytokine TGF-β in HaCaT human transformed keratinocytes (Hannon and Beach 1994). The p15 and p16 genes reside next to each other on human chromosome 9p21, at or near a familial melanoma predisposition locus (Kamb et al. 1994). p16 is deleted or mutated in a high proportion of primary esophageal squamous cell carcinomas (Mori et al. 1994) and sporadic pancreatic adenocarcinomas (Caldas et al. 1994), substantiating the idea that this is a tumor suppressor gene (Kamb et al. 1994).

The other CDI family includes p21$^{CIP1}$ (a.k.a. WAF1, SDI1 or CAP20) (El-Deiry et al. 1993; Gu et al. 1993; Harper et al. 1993; Noda et al. 1994; Xiong et al. 1993) and p27$^{KIP1}$ (Polyak et al. 1994b; Toyoshima and Hunter 1994), two proteins structurally unrelated to the INK4s. In vitro, p21 and p27 have broad specificity, inhibiting the kinase activity of preactivated cyclin E-cdk2, cyclin D-cdk4, the S phase CDK cyclin A-cdk2 and, to a lesser extent, the mitotic CDK cyclin B-Cdc2 (Gu et al. 1993; Harper et al. 1993; Polyak et al. 1994b; Toyoshima and Hunter 1994; Xiong et al. 1993). p27 does not inhibit CAK directly (Kato et al. 1994; Nourse et al. 1994), however, it binds to CDK complexes preventing their phosphorylation and activation by CAK (Polyak et al. 1994a; Polyak et al. 1994b). When overexpressed in transfected cells, p21 and p27 cause $G_1$ arrest, suggesting that despite their broad specificity in vitro, these CDIs may act only on $G_1$ CDKs in vivo (El-Deiry et al. 1993; Harper et al. 1993; Polyak et al. 1994b; Toyoshima and Hunter 1994).

p21 and p27 participate in numerous regulatory responses. The $G_1$ arrest that follows radiation-induced DNA damage, ostensibly to allow for DNA repair, is mediated by the tumor suppressor p53 which elevates p21 levels transcriptionally, leading to CDK inhibition (El-Deiry et al. 1994; El-Deiry et al. 1993). Mitogen-induced emergence from quiescence occurs with induction of p21 expression, suggesting that cycling cells may need p21 as a regulatory device (Li et al. 1994a; Nourse et al. 1994). In vitro binding of one p21 molecule to a CDK complex stimulates kinase activity, the inhibitory effect appearing only when a second p21 molecule binds to this complex (Zhang et al. 1994). Thus, p21 might act as both a positive and a negative regulator of CDKs in vivo. In addition, p21 but not p27 can inhibit processive DNA replication by binding to proliferating cell nuclear antigen (PCNA), a polymerase δ subunit (Flores-Rozas et al. 1994; Waga et al. 1994). p27 expression is high in contact-inhibited or mitogen-deprived cells (Polyak et al. 1994a) and, in contrast to p21 expression, it often declines upon mitogen-induced exit from quiescence (Kato et al. 1994; Nourse et al. 1994). Various antimitogens including cAMP in macrophages (Kato et al. 1994) and rapamycin in T-lymphocytes (Nourse et al. 1994) prevent mitogen-induced p27 down-regulation, thus inhibiting CDK activation and $G_1$ progression. p27 can also act as a passive instrument of antimitogenic action, as in the case of Mv1Lu lung epithelial cells. In these cells, TGF-β down-regulates cdk4 (Ewen et al. 1993), thus lowering the total CDK pool presumably below the threshold imposed by a fixed p27 level (Polyak et al. 1994a).

Despite their recent identification, it is clear that the CDIs play a pivotal role in cell cycle control. Their nature as putative tumor suppressor genes has important implications for diagnosis and treatment of hyperproliferative disorders. Furthermore, the known CDIs are notorious for their structural and functional diversity, suggesting that they may be but the first identified examples of a larger group whose components have highly specialized structure and function. Given this possibility, applicants searched for additional members of the p21/p27 family. Applicants have isolated a new member of the p21$^{CIP1}$/p27$^{KIP1}$ CDI family and named it p57$^{KIP2}$ to denote its apparent molecular mass and higher similarity to p27$^{KIP1}$. Three distinct p57 cDNAs were cloned that differ at the start of their open reading frames and correspond to messages generated by the use of distinct splice acceptor sites. p57 is distinguished from p21 and p27 by its unique domain structure. Four distinct domains follow the heterogeneous N-terminal region and include, in order, a p21/p27-related CDK inhibitory domain, a proline-rich (28% proline) domain, an acidic (36% glutamic or aspartic acid) domain, and a C-terminal nuclear targeting domain that contains a putative CDK phosphorylation site and has sequence similarity to p27 but not to p21. Most of the acidic domain consists of a novel, tandemly repeated four-amino acid motif. p57 is a potent inhibitor of G1 and S phase CDKs (cyclin E-cdk2, cyclin D2-cdk4 and cyclin A-cdk2) and, to lesser extent, of the mitotic cyclin B-Cdc2. In mammalian cells, p57 localizes to the nucleus, associates with G1 CDK components, and its overexpression causes a complete cell cycle arrest in G1 phase. In contrast to the widespread expression of p21 and p27 in human tissues, p57 is expressed in a tissue-specific manner, as a 1.5 kb species in placenta and at lower levels in various other tissues, and a 7 kb mRNA species observed in skeletal muscle and heart. The expression pattern and unique domain structure of p57 suggest that this CDI may play a specialized role in cell cycle control.

SUMMARY OF THE INVENTION

This invention provides an isolated nucleic acid molecule encoding a mammalian $p57^{KIP2}$. This invention also provides vectors comprising the isolated nucleic acid molecule encoding a mammalian $p57^{KIP2}$. This invention further provides a host vector system for the production of a mammalian $p57^{KIP2}$. This invention also provides probes for the isolated nucleic acid molecule encoding a mammalian $p57^{KIP2}$. This invention provides antibodies directed against a mammalian $p57^{KIP2}$. This invention also provides transgenic animals comprising isolated nucleic acid molecules encoding a mammalian $p57^{KIP2}$. Finally, this invention provides different uses of the mammalian $p57^{KIP2}$.

This invention provides a method of determining whether an agent is capable of specifically inhibiting the ability of $p57^{KIP2}$ to inhibit the activation of cyclin-Cdk complex which comprises: (a) contacting suitable amounts of $p57^{KIP2}$, a cyclin Cdk and the agent under suitable conditions; (b) subjecting the $p57^{KIP2}$, cyclin, Cdk, and agent so contacted to conditions which would permit the formation of active cyclin-Cdk complex in the absence of $p57^{KIP2}$; (c) quantitatively determining the amount of active cyclin-Cdk complex so formed; and (d) comparing the amount of active cyclin-Cdk complex so formed with the amount of active cyclin E-Cdk2 complex formed in the absence of the agent, a greater amount of active cyclin-Cdk complex formed in the presence of the agent than in the absence of the agent indicating that the agent is capable of specifically inhibiting the ability of $p57^{KIP2}$ to inhibit the activation of cyclin-Cdk complex.

This invention provides a method of determining whether an agent is capable of specifically enhancing the ability of $p57^{KIP2}$ to inhibit the activation of cyclin-Cdk complex which comprises: (a) contacting suitable amounts of $p57^{KIP2}$, cyclin, a Cdk and the agent under suitable conditions; (b) subjecting the $p57^{KIP2}$, cyclin, Cdk, and agent so contacted to conditions which would permit the formation of active cyclin-Cdk complex in the absence of $p57^{KIP2}$; (c) quantitatively determining the amount of active cyclin-Cdk complex so formed; and (d) comparing the amount of active cyclin-Cdk complex so formed with the amount of active cyclin-Cdk complex formed in the absence of the agent, a lesser amount of active cyclin-Cdk complex formed in the presence of the agent than in the absence of the agent indicating that the agent is capable of specifically enhancing the ability of $p57^{KIP2}$ to inhibit the activation of cyclin-Cdk complex.

This invention provides a method of treating a subject having a hyperproliferative disorder which comprises administering to the subject a therapeutically effective amount of an agent capable of specifically enhancing the ability of $p57^{KIP2}$ to inhibit the activation of cyclin-Cdk complex in the hyperproliferative cells of the subject, so as to thereby treat the subject.

This invention provides a method of treating a subject having a hypoproliferative disorder which comprises administering to the subject a therapeutically effective amount of an agent capable of specifically inhibiting the ability of $p57^{KIP2}$ to inhibit the activation of cyclin-Cdk complex in the hypoproliferative cells of the subject, so as to thereby treat the subject.

This invention provides a method of diagnosing a hyperproliferative disorder in a subject which disorder is associated with the presence of a $p57^{KIP2}$ mutation in the cells of the subject, which comprises determining the presence of a $p57^{KIP2}$ mutation in the cells of the subject, said mutation being associated with a hyperproliferative disorder, so as to thereby diagnose a hyperproliferative disorder in the subject.

This invention provides a pharmaceutical composition which comprises an effective amount of a recombinant virus capable of infecting a suitable host cell, said recombinant virus comprising the nucleic acid molecule of a DNA molecule of an isolated nucleic acid molecule encoding a mammalian $p57^{KIP2}$, and a pharmaceutically acceptable carrier.

This invention provides a method for treating a subject suffering from a hyperproliferative disorder associated with the presence of a $p57^{KIP2}$ mutation in the cells of the subject, which comprises administering to the subject an amount of the pharmaceutical composition of claim 50 effective to treat the subject.

BRIEF DESCRIPTION OF THE FIGURES

FIGS. 1A and 1B Nucleic acid and amino acid sequences of $p57^{KIP2}$.

A, Nucleotide sequence of $p57^{KIP2}$ (Sequence I.D. No.:14). The open reading frame starts at position 41 and ends at position 1353.

B, Coding sequence of $p57^{KIP2}$ (Sequence I.D. No.:15).

FIGS. 2A and 2B $p57^{KIP2}$ amino acid sequence and comparison with $p27^{KIP1}$ and $p21^{CiP1/WAF1}$.

A, Sequence alignment of mouse $p57^{KIP2}$, mouse $p27^{KIP1}$ (Polyak et al. 1994b) and mouse $p21^{Cip1/WAF1}$ (Huppi et al. 1994). Identical amino acids are indicated by boxes. Acidic amino acid residues at the start of tandemly repeated four-amino acid motifs are indicated by dots. A putative nuclear localization signal is underlined in each protein. CDK kinase consensus phosphorylation sites in p57 and p27 (CDK) and a MAP kinase consensus phosphorylation site in p57 (MAPK) are indicated. Numbers indicate amino acid residues.

B, Schematic representation of p57, p27 and p21 protein domain structures. The three proteins contain a region of similarity (stippled box) that corresponds the CDK inhibitory domain in p27 (Polyak et al. 1994b). p57 contains a proline-rich domain (open thick box) partially overlapping with an acidic domain (gray box). Putative nuclear localization signals (closed boxes) and Cdc2 consensus phosphorylation site (CDK) are indicated. Numbers indicate amino acid residues.

Figure 3:
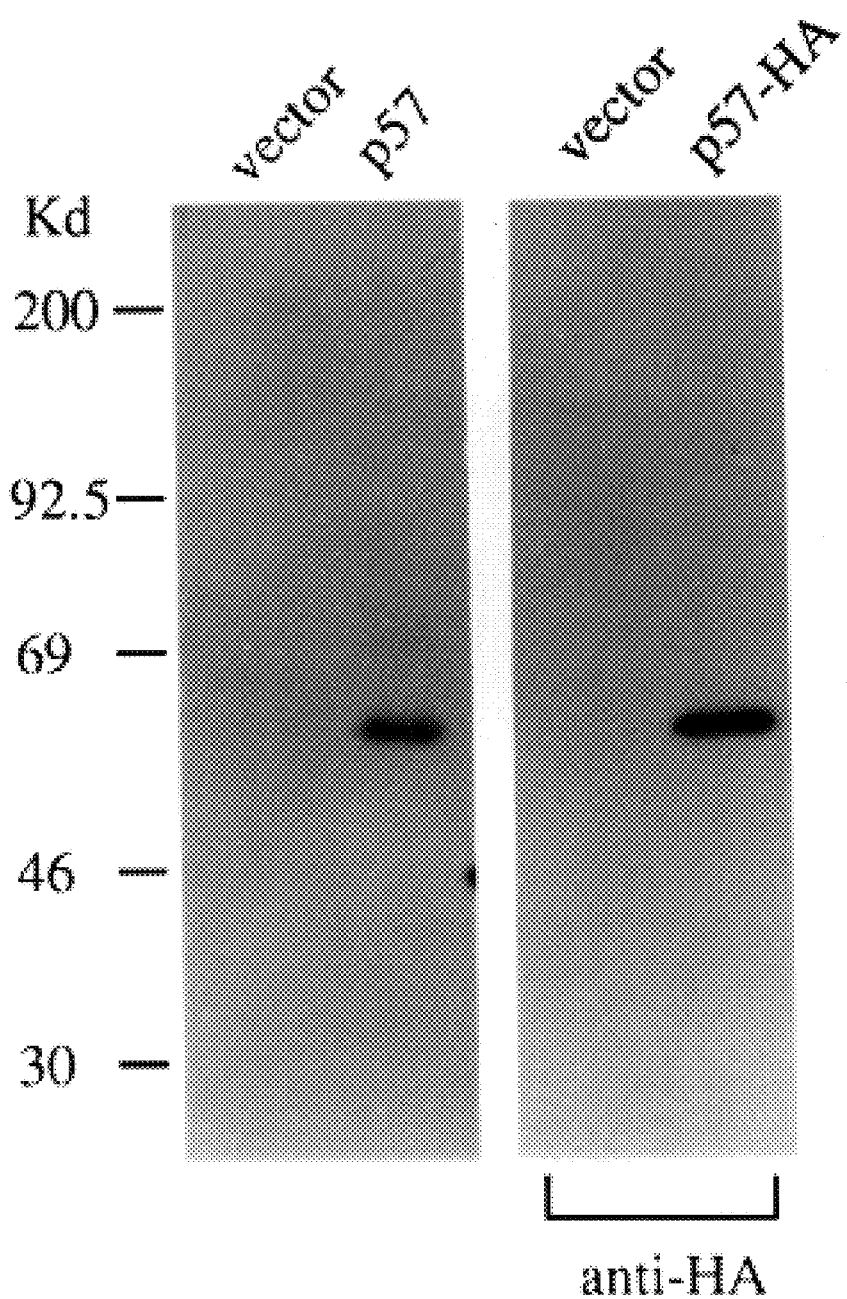

FIG. 3 In vitro translation of $p57^{KIP2}$. Vector encoding p57 (p57), p57 tagged with the HA epitope at the C-terminus (p57-HA) or empty vector (vector) were transcribed in vitro and the resulting RNA translated in the presence of $^{35}$S-methionine. The entire in vitro translation mixture, or a precipitate with HA antibody (anti-HA) were subjected to SDS-PAGE and fluorography.

Figure 4:
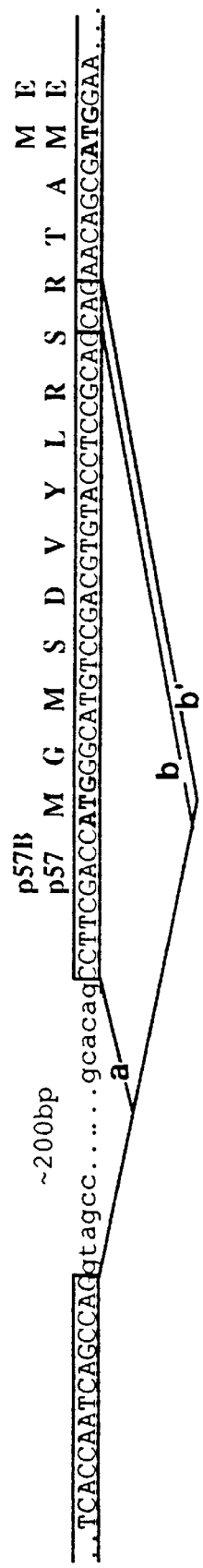
Figure 5A:
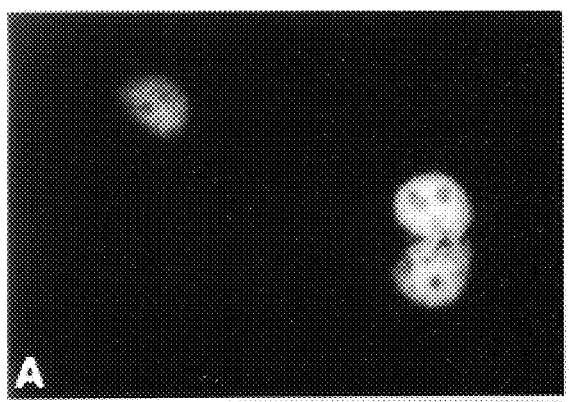
Figure 5B:
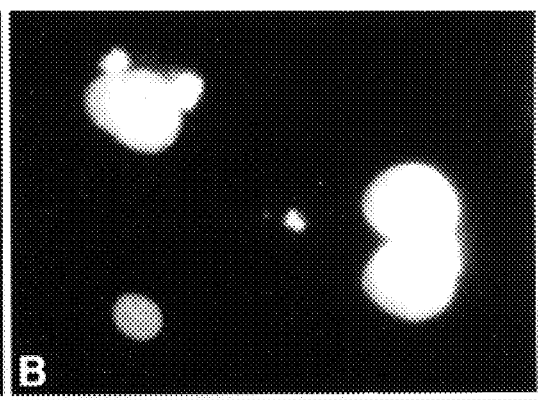
Figure 5C:
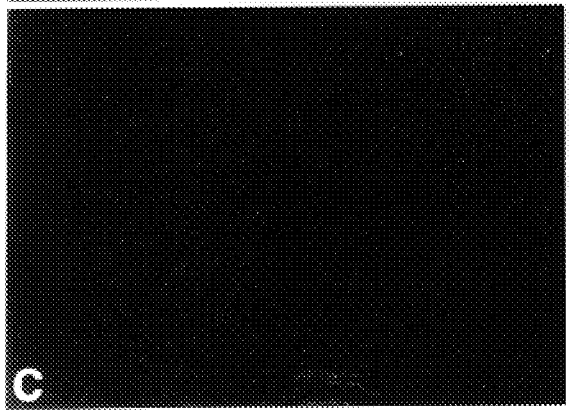
Figure 5D:
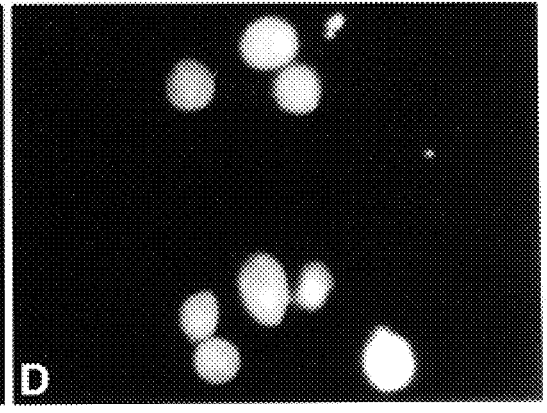

FIG. 4 Origin of three $p57^{KIP2}$ cDNA species Three distinct mouse p57 cDNA clones include the sequence shown in the left box continued with sequences shown in the right box starting at points designated a, b and b', respectively. The remainder of these clones were identical. Two PCR primers flanking the deleted region (see 'Experimental Procedures') were used to amplify mouse genomic DNA, yielding a product ~200 bp longer than expected from an intronless genomic region. The ends of the intervening sequence show typical features of an intron including a 5' splice donor site, $(TC)_n$ tracks (not shown) and a 3' splice acceptor site. Splicing at positions b and b' results from the use of alternative acceptor sites. The b and b' splicing events eliminate a region containing the first methionine codon, which is in an optimal translation initiation context (Kozak 1986), and yield an open reading frame with a potential translation start site 13 amino acids downstream of the start site in full length p57.

FIGS. 5A, 5B, 5C and 5D Nuclear localization of p57. R-1B/L17 cells transiently transfected with a p57-HA vector (A and B) or empty vector (C and D) were stained with anti-HA mouse monoclonal antibody followed by rhodamine-conjugated anti-mouse Ig antibody. COS-1 cells transiently transfected with a flag-p57 vector (E and F) or empty vector (G and H) were stained with anti-flag mouse monoclonal antibody followed by fluorescein-conjugated anti-mouse Ig antibody. Indirect immunofluorescence is shown at high magnification (A, C, E, G). The same cells were stained with DAPI to visualize nuclear DNA (B, D, F, H). Note that two of the cells shown in panel A (arrows) have nuclear staining whereas cells transfected with empty vector in panel C exclude staining from the nucleus.

FIGS. 6A and 6B Association of p57 CDK components in mammalian cells.

A, R-1B/L17 cells were transiently transfected with empty vector (pCMV5), flag-p57 vector, or were mock transfected (–). Lysates from $^{35}$S-methionine labeled cells were precipitated with flag antibody and displayed by electrophoresis and fluorography. A specific band of 57 kD corresponding to p57 (arrow) and various specifically coprecipitating bands are observed.

B, Cells transiently transfected with empty pCMV5 or flag-p57 vector were lysed and precipitated with flag antibody. Immunoprecipitates were resolved by SDS-PAGE and blotted with the indicated antibodies against G1 CDK components, demonstrating the presence of these components in these p57 precipitates.

FIGS. 7A, 7B, 7C-1–7C-6 Inhibition of CDK kinase activity in vitro. Insect cell lysates containing the indicated baculovirally expressed cyclin-cdk combinations were assayed for histone H1 kinase activity (A) and Rb kinase activity (B) in the presence of the indicated concentrations of bacterially produced p57 or p27. Phosphorylation reactions were stopped by boiling in SDS-PAGE sample buffer and resolved by electrophoresis. Autoradiograms show the phosphorylated histone H1 band (A) and Rb band (B). The signal associated with these bands was quantitated in a Phosphorimager and is plotted (C) as percent relative to samples that did not receive inhibitors.

Figure 8:
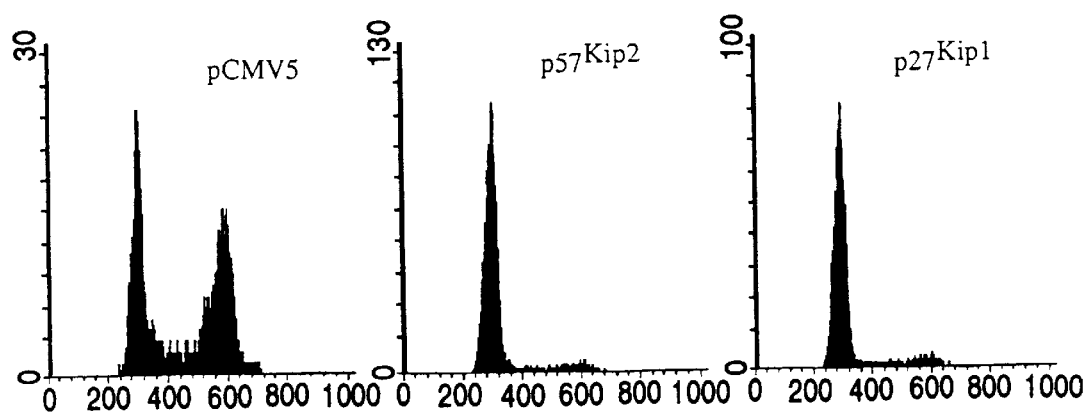

FIG. 8 p57 overexpression blocks entry into S phase. R-1B/L17 cells were transiently cotransfected with CD16 and either empty pCMV5 vector, p57 vector or p27 vector. Two days after transfection, cells were stained with anti-CD16 and the CD16$^+$ population collected in a cell sorter and subjected to flow cytometry to determine its cell cycle distribution according to DNA content (Top panel). The percent distribution in different cell cycle compartments is shown for each transfectant. $^{125}$I-deoxyuridine incorporation assays were done 48 h posttransfection, and the results are presented as the average±S.D. of triplicate determinations.

FIGS. 9A and 9B Expression pattern of p57 and p27 in various human tissues. A blot that contains equal amounts of poly(A)$^+$ RNA from the indicated human tissues and was previously hybridized with a p27 cDNA probe (Polyak et al., 1994b; reprinted with permission of the copyright holder, Cell Press) is shown (9A) together with the results of stripping the same blot and reprobing it with a p57 probe (9B).

FIG. 10 Human p57$^{KIP2}$ partial sequence (Sequence I.D. No.:11).

Figure 11:
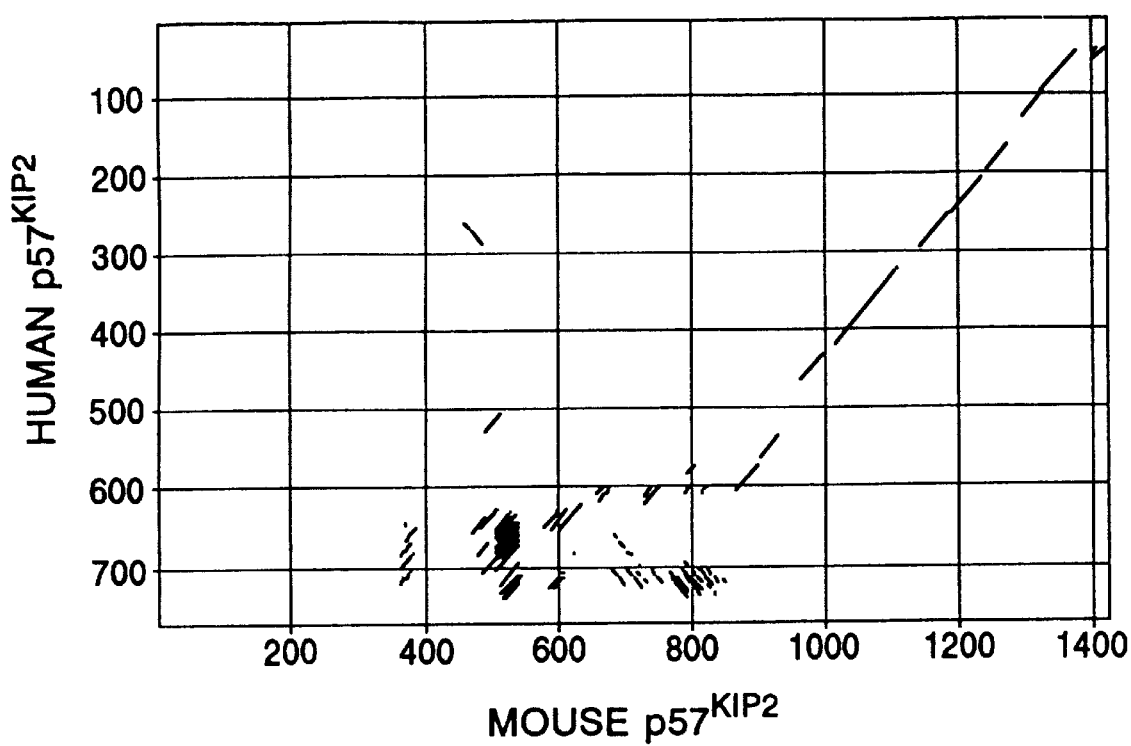

FIG. 11 Matrix plot of human p57$^{KIP2}$ and mouse p57$^{KIP2}$. The matrix plot shows that the human clone of p57$^{KIP2}$ shares high homology with mouse p57$^{KIP2}$ at the DNA level.

DETAILED DESCRIPTION OF THE INVENTION

This invention provides an isolated nucleic acid molecule encoding a mammalian p57$^{KIP2}$. In one embodiment, the nucleic acid molecule is a DNA molecule. The DNA molecule may be a cDNA molecule, a cloned genomic DNA molecule or a synthetic DNA. In another embodiment, the nucleic acid molecule is an RNA molecule. The RNA molecule may be an mRNA molecule.

In a separate embodiment, this invention provides an isolated nucleic acid molecule encoding a mouse p57$^{KIP2}$. In a further embodiment, the isolated nucleic acid molecule comprises the sequence disclosed in FIG. 1A. This invention also provides an isolated nucleic acid molecule encoding a human p57$^{KIP2}$. In a further embodiment, the isolated nucleic acid molecule comprises the sequence disclosed in FIG. 10.

One means of isolating a mammalian p57$^{KIP2}$ is to probe a mammalian genomic library with a natural or artificially designed DNA probe, using methods well known in the art. In one embodiment of this invention, the nucleic acid molecules encoding the human p57$^{KIP2}$ are isolated from a human cDNA library using probes derived from the mouse DNA sequences.

In an embodiment, mouse cDNA of p57$^{KIP2}$ was used to screen a human kidney cDNA library. The positive clones identified were subcloned into RI site of the plasmid PBSKII for determination of DNA sequence.

This invention also provides a vector comprising the recombinant nucleic acid molecule providing a cDNA molecule encoding a mammalian p57$^{KIP2}$. In an embodiment, the vector is a plasmid. In a further embodiment, the plasmid is designated as pMH115 (ATCC Accession No. 97100). In a still further embodiment, the plasmid is designated as pMH178 (ATCC Accession No. 97101).

Plasmid pMH115 contains p57$^{KIP2}$ mouse cDNA and ampicillin resistance gene. Plasmid DNA can be transformed into DH5α E. coli for amplification and selected with ampicillin. Purified plasmids may be digested wtih restriction enzyme EcoRI and HinkIII to excise the 1.6 kilobase pairs insert of p57$^{KIP2}$ mouse cDNA.

This plasmid pMH115 was deposited on Mar. 17, 1995 with the American Type Culture Collection (ATCC), 12301 Parklawn Drive, Rockville, Md., 20852, U.S.A. under the provisions of the Budapest Treaty for the International Recognition of the Deposit of Microorganisms for the Purposes of Patent Procedure. pMH115 was accorded ATCC Accession No. 97100.

Plasmid pMH178 contains p57$^{KIP2}$ human cDNA and ampicillin resistance gene. The plasmid may be transformed into DH5α E. coli for amplification and selected with ampicillin. Purified plasmids may be digested with XhoI and XbaI to excise the p57$^{KIP2}$ cDNA insert which is approximately seven hundred basepairs.

This plasmid pMH178 was deposited on Mar. 17, 1995 with the American Type Culture Collection (ATCC), 12301 Parklawn Drive, Rockville, Md., 20852, U.S.A. under the provisions of the Budapest Treaty for the International Recognition of the Deposit of Microorganisms for the Purposes of Patent Procedure. pMH178 was accorded ATCC Accession No. 97101.

The subject invention further provides a vector comprising the recombinant nucleic acid molecule of the subject invention. In one embodiment, the vector is a plasmid. In another embodiment, the vector is a virus.

In accordance with the invention, various vector systems for expression of the protein of the subject invention may be employed. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

The subject invention further provides a host vector system for the production of a mammalian p57$^{KIP2}$ which comprises the vector of the subject invention in a suitable host.

In one embodiment, the suitable host is a bacterial cell. In another embodiment, the suitable host is an eucaryotic cell. The eucaryotic cell may be an insect cell. Insect cells include, by way of example, Sf9 cells. In another embodiment, the suitable host is a mammalian cell.

This invention provides a nucleic acid probe comprising a nucleic acid molecule of at least 15 nucleotides capable of specifically hybridizing with a unique sequence included within the sequence of the nucleic acid molecule of an isolated nucleic acid molecule encoding a mammalian p57$^{KIP2}$. In an embodiment, this invention provides a DNA probe. In another embodiment, this invention provides an RNA probe.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the mammalian p57$^{KIP2}$.

Nucleic acid probe technology is well known to those skilled in the art who will readily appreciate that such probes may vary in length and may be labeled with a detectable label, such as a radioisotope or fluorescent dye, to facilitate detection of the probe. Detection of nucleic acid molecules encoding the p57$^{KIP2}$ is useful as a diagnostic test for any disease process in which levels of expression of the corresponding p57$^{KIP2}$ is altered. DNA probe molecules are produced by insertion of a DNA molecule which encodes p57$^{KIP2}$ or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. The probes are useful for 'in situ' hybridization, or for other hybridization assays for the presence of these genes or their mRNA in various biological tissues.

In addition, synthesized oligonucleotides (produced by a DNA synthesizer) complementary to the sequence of a DNA molecule which encodes a p57$^{KIP2}$ are useful as probes for this gene, for its associated mRNA, or for the isolation of related genes by homology screening of genomic or cDNA libraries, or by the use of amplification techniques such as the Polymerase Chain Reaction.

This invention provides a purified mammalian p57$^{KIP2}$. In an embodiment, the purified p57$^{KIP2}$ is a human p57$^{KIP2}$. In another embodiment, the purified p57$^{KIP2}$ is a mouse p57$^{KIP2}$. In a further embodiment, the purified p57$^{KIP2}$ comprises the amino acid sequence recited in FIG. 1B.

This invention provides a purified unique polypeptide fragment of the mammalian p57$^{KIP2}$. In an embodiment, it is a unique fragment of the human p57$^{KIP2}$. In another embodiment, it is a unique fragment of the mouse p57$^{KIP2}$.

As used herein, the term "unique polypeptide fragment" encompasses any polypeptide with the amino acid sequence specific only to the mammalian p57$^{KIP2}$.

One means for obtaining an isolated polypeptide fragment of a p57$^{KIP2}$ is to treat isolated p57$^{KIP2}$ with commercially available peptidases and then separate the polypeptide fragments using methods well known to those skilled in the art. Polypeptide fragments are often useful as antigens used to induce an immune response and subsequently generate antibodies against the polypeptide fragment and possibly the whole polypeptide.

As used herein, the term "purified protein" is intended to encompass a protein molecule free of other cellular components. One means for obtaining purified mammalian p57$^{KIP2}$ is to express DNA encoding the p57$^{KIP2}$ in a suitable host, such as a bacterial, yeast, insect, or mammalian cell, using methods well known to those skilled in the art, and recovering the p57$^{KIP2}$ after it has been expressed in such a host, again using methods well known in the art. The p57$^{KIP2}$ may also be isolated from cells which express the p57$^{KIP2}$, in particular from cells which have been transfected with the expression vectors described below in more detail.

This invention provides an antibody directed to a purified mammalian p57$^{KIP2}$ of a purified mammalian p57$^{KIP2}$. This invention also provides an antibody capable of specifically recognizing a mammalian p57$^{KIP2}$.

This invention provides an antibody capable of specifically recognizing a human p57$^{KIP2}$. This invention also provides an antibody capable of specifically recognizing a mouse p57$^{KIP2}$, wherein the p57$^{KIP2}$. In an embodiment, the antibody is monoclonal.

Antibodies directed to a mammalian p57$^{KIP2}$ may be serum-derived or monoclonal and are prepared using methods well known in the art.

The subject invention further provides a method for obtaining partially purified polyclonal antibodies capable of specifically binding to p57$^{KIP2}$ protein which method comprises (a) immunizing a subject with p57$^{KIP2}$, (b) recovering from the immunized subject serum comprising antibodies capable of specifically binding to p57$^{KIP2}$, and (c) partially purifying the antibodies present in the serum, thereby obtaining partially purified polyclonal antibodies capable of specifically binding to p57$^{KIP2}$.

As used herein, partially purified antibodies means a composition which comprises antibodies which specifically bind to p57$^{KIP2}$, and consists of fewer protein impurities than does the serum from which the antibodies are derived. A protein impurity means a protein other than the antibodies specific for p57$^{KIP2}$ protein. For example, the partially purified antibodies might be an IgG preparation.

Methods of recovering serum from a subject are well known to those skilled in the art. Methods of partially purifying antibodies are also well known to those skilled in the art, and include, by way of example, filtration, ion exchange chromatography, and precipitation.

The subject invention further provides the partially purified antibodies produced by the method of the subject invention.

The subject invention further provides a method for obtaining a purified monoclonal antibody capable of specifically binding to p57$^{KIP2}$ which method comprises (a) immunizing a subject with p57$^{KIP2}$ protein, (b) recovering from the immunized subject a B cell-containing cell sample, (c) contacting the B cell-containing cell sample so recovered with myeloma cells under conditions permitting fusion of the myeloma cells with the B cells therein so as to form hybridoma cells, (d) isolating from the resulting sample a hybridoma cell capable of producing a monoclonal antibody capable of specifically binding to p57$^{KIP2}$, (e) growing the hybridoma cell so isolated under conditions permitting the production of the monoclonal antibody, and (f) recovering the monoclonal antibody so produced, thereby obtaining a purified monoclonal antibody capable of specifically binding to p57$^{KIP2}$. Methods of making hybridomas and monoclonal antibodies are well known to those skilled in the art.

The subject invention further provides the hybridoma cell produced in step (d) of the method of the subject invention.

The subject invention further provides the purified monoclonal antibody produced by the method of the subject invention.

As used herein, a "purified monoclonal antibody" means the monoclonal antibody free of any other antibodies.

The subject invention further provides an antibody capable of specifically binding to p57$^{KIP2}$ protein, said antibody being labeled with a detectable marker.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

These antibodies are useful to detect the presence of mammalian p57$^{KIP2}$ encoded by the isolated DNA, or to inhibit the function of the p57$^{KIP2}$ in living animals, in humans, or in biological tissues or fluids isolated from animals or humans.

This invention provides a transgenic nonhuman mammal which comprises an isolated DNA molecule of a DNA molecule encoding a mammalian p57$^{KIP2}$.

This invention provides a transgenic nonhuman mammal which comprises an isolated DNA molecule encoding a vertebrate p57$^{KIP2}$.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a vertebrate p57$^{KIP2}$ is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a method of determining the physiological effects of expressing varying levels of mammalian p57$^{KIP2}$ which comprises producing a panel of transgenic nonhuman animals each expressing a different amount of a mammalian p57$^{KIP2}$.

This invention provides a method for producing a mammalian p57$^{KIP2}$ which comprises growing the host vector system comprising the recombinant nucleic acid molecule providing a cDNA molecule encoding a mammalian p57$^{KIP2}$ under conditions permitting the production of the protein and recovering the protein produced thereby.

The subject invention further provides a method for producing a mammalian p57$^{KIP2}$, which comprises growing the host vector system of the subject invention under conditions permitting the production of the protein and recovering the protein produced thereby.

Methods and conditions for growing host vector systems and for recovering the protein so produced are well known to those skilled in the art, and may be varied or optimized depending upon the specific vector and host cell employed. Such recovery methods include, by way of example, gel electrophoresis, ion exchange chromatography, affinity chromatography or combinations thereof.

This invention provides a method of determining whether an agent is capable of specifically inhibiting the ability of p57$^{KIP2}$ to inhibit the activation of cyclin E-Cdk2 complex which comprises: (a) contacting suitable amounts of p57 protein, a cyclin, a Cdk and the agent under suitable conditions; (b) subjecting the p57, the cyclin, the Cdk, and agent so contacted to conditions which would permit the formation of active cyclin-Cdk complex in the absence of p57$^{KIP2}$; (c) quantitatively determining the amount of active cyclin-Cdk complex so formed; and (d) comparing the amount of active cyclin-Cdk complex so formed with the amount of active cyclin-Cdk complex formed in the absence of the agent, a greater amount of active cyclin-Cdk complex formed in the presence of the agent than in the absence of the agent indicating that the agent is capable of specifically inhibiting the ability of p57$^{KIP2}$ to inhibit the activation of cyclin-Cdk complex. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

As used herein, the term "agent" includes both protein and non-protein moieties. In one embodiment, the agent is a small molecule. In another embodiment, the agent is a protein. The agent may be derived from a library of low molecular weight compounds or a library of extracts from plants or other organisms.

In the subject invention, an agent capable of specifically inhibiting the ability of p57$^{KIP2}$ to inhibit the activation of cyclin-Cdk complex interferes with the interaction between p57$^{KIP2}$ and cyclin-Cdk complex, but not with the site-specific phosphorylation of the Cdk moiety of the cyclin-Cdk complex in the absence of p57$^{KIP2}$.

The cyclin-Cdk complex includes, but is not limited to, cuyclinE-Cdk2 complex, cyclinA-Cdk2, cyclinD-Cdk4, cyclinD-Cdk5 and cyclinD-Cdk6.

The cyclins may be obtained using methods well known to those skilled in the art based on the nucleic acid sequence encoding same. For example, the nucleic acid sequence encoding CyclinE was disclosed in Koff, et al. (1991).

Cdks may be obtained using methods well known to those skilled in the art. For example, Cdk2's nucleic acid sequence encoding same was disclosed in Elledge and Spottswood (1991).

Amounts of p57$^{KIP2}$, cyclin, Cdk and the agent suitable for the method of the subject invention may be determined by methods well known to those skilled in the art. An example of suitable conditions (i.e., conditions suitable for measuring the effect on p57$^{KIP2}$ function by an agent) under which p57$^{KIP2}$, cyclin, Cdk and the agent are contacted appears infra.

An example of conditions which would permit the formation of active cyclin-Cdk complex in the absence of p57$^{KIP2}$ protein also appears infra.

As used herein, "active cyclin-Cdk complex" means a cyclin-Cdk complex which is capable of specifically phosphorylating a suitable substrate (e.g., histone H1). An example of an active cyclin-Cdk complex is provided infra. The amount of active cyclin-Cdk complex correlates with its measurable activity. Thus, quantitatively determining the amount of active cyclin-Cdk complex may be accomplished by measuring the rate at which a substrate of the active cyclin-Cdk complex is phosphorylated. Such methods well known to those skilled in the art, and include, by way of example, a histone H1 kinase assay.

In the method of the subject invention, the cyclin and Cdk proteins may exist as separate proteins, or as a complex, prior to being contacted with the agent.

This invention provides a method of determining whether an agent is capable of specifically enhancing the ability of p57$^{KIP2}$ protein to inhibit the activation of cyclin-Cdk complex which comprises: (a) contacting suitable amounts of p57$^{KIP2}$ protein, cyclin, Cdk and the agent under suitable conditions; (b) subjecting the p57$^{KIP2}$, cyclin, Cdk, and agent so contacted to conditions which would permit the formation of active cyclin-Cdk complex in the absence of p57$^{KIP2}$ protein; (c) quantitatively determining the amount of active cyclin-Cdk complex so formed; and (d) comparing the amount of active cyclin-Cdk complex so formed with the amount of active cyclin-Cdk complex formed in the absence of the agent, a lesser amount of active cyclin-Cdk complex formed in the presence of the agent than in the absence of the agent indicating that the agent is capable of specifically enhancing the ability of p57$^{KIP2}$ protein to inhibit the activation of cyclin-Cdk complex. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

In the subject invention, an agent capable of specifically enhancing the ability of p57$^{KIP2}$ protein to inhibit the activation of cyclin-Cdk complex affects the interaction between p57$^{KIP2}$ protein and cyclin-Cdk complex, but not with the site-specific phosphorylation of the Cdk moiety of the cyclin-Cdk complex in the absence of p57$^{KIP2}$ protein.

This invention provides a method of treating a subject having a hyperproliferative disorder which comprises administering to the subject a therapeutically effective amount of an agent capable of specifically enhancing the ability of p57$^{KIP2}$ protein to inhibit the activation of cyclin-Cdk complex in the hyperproliferative cells of the subject, so as to thereby treat the subject. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

In the preferred embodiment, the subject is a human.

A hyperproliferative disorder is a disorder wherein cells present in the subject having the disorder proliferate at an abnormally high rate, which abnormally high rate of proliferation is a cause of the disorder. In one embodiment, the hyperproliferative disorder is selected from the group consisting of cancer and hyperplasia.

The administering of the agent may be effected or performed using any of the various methods known to those skilled in the art. In one embodiment, the administering comprises administering intravenously. In another embodiment, the administering comprises administering intramuscularly. In yet another embodiment, the administering comprises administering subcutaneously. In still another embodiment, the administering comprises administering orally.

The therapeutically effective amount of the agent may be determined by methods well known to those skilled in the art.

The subject invention further provides a pharmaceutical composition comprising a therapeutically effective amount of an agent capable of specifically enhancing the ability of p57$^{KIP2}$ to inhibit the activation of cyclin-Cdk complex in the hyperproliferative cells of a subject suffering from a hyperproliferative disorder, and a pharmaceutically acceptable carrier. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The subject invention further provides a method of treating a subject having a hyperproliferative disorder which comprises administering to the subject a therapeutically effective amount of an agent capable of mimicking the ability of $p57^{KIP2}$ protein to inhibit the activation of cyclin Cdk complex in the hyperproliferative cells of the subject, so as to thereby treat the subject. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

The subject invention further provides a method of treating a subject having a hypoproliferative disorder which comprises administering to the subject a therapeutically effective amount of an agent capable of specifically inhibiting the ability of $p57^{KIP2}$ protein to inhibit the activation of cyclin-Cdk complex in the hypoproliferative cells of the subject, so as to thereby treat the subject.

In the preferred embodiment, the subject is a human.

A hypoproliferative disorder is a disorder wherein cells present in the subject having the disorder proliferate at an abnormally low rate, which abnormally low rate of proliferation is a cause of the disorder. In one embodiment, the hypoproliferative disorder is an ulcer. Examples of hypoproliferative cells are terminally differentiated cells in normal tissue and organs which, with the exception of the liver and bone marrow, normally lack the ability to regenerate following traumatic injury. Thus, the method of the subject invention, and agents identified thereby, have use in stimulating tissue and organ repair in subjects in need thereof, as well as in establishing tissue cultures of cells from a variety of different tissues.

The therapeutically effective amount of the agent may be determined by methods well known to those skilled in the art.

The subject invention further provides a pharmaceutical composition comprising a therapeutically effective amount of an agent capable of specifically inhibiting the ability of $p57^{KIP2}$ protein to inhibit the activation of cyclin-Cdk complex in the hypoproliferative cells of a subject suffering from a hypoproliferative disorder, and a pharmaceutically acceptable carrier. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

The subject invention further provides a method for quantitatively determining the amount of $p57^{KIP2}$ in a sample which comprises contacting the sample with the antibody of the subject invention under conditions permitting the antibody to form a complex with $p57^{KIP2}$ protein present in the sample, quantitatively determining the amount of complex so formed, and comparing the amount so determined with a known standard, so as to thereby quantitatively determine the amount of $p57^{KIP2}$ in the sample.

The sample may be, for example, a cell sample, tissue sample, or protein-containing fluid sample. Conditions permitting an antibody to form a complex with its antigen and methods of detecting the presence of complex so formed are well known in the art.

The amount of $p57^{KIP2}$ protein present in a sample as determined need not be an absolute number, in the sense that it need not be the actual number of $p57^{KIP2}$ protein molecules or moles of $p57^{KIP2}$ protein in the sample. Rather, the amount determined may merely correlate with this number.

The subject invention further provides a method for quantitatively determining the level of expression of $p57^{KIP2}$ in a cell population, and a method for determining whether an agent is capable of increasing or decreasing the level of expression of $p57^{KIP2}$ in a cell population. The method for determining whether an agent is capable of increasing or decreasing the level of expression of $p57^{KIP2}$ in a cell population comprises the steps of (a) preparing cell extracts from control and agent-treated cell populations, (b) isolating $p57^{KIP2}$ from the cell extracts (e.g., by affinity chromatography on, and elution from, a cyclin-Cdk complex solid phase affinity adsorbent), (c) quantifying (e.g., in parallel) the amount of $p57^{KIP2}$ inhibitor activity in the control and agent-treated cell extracts using a cyclin Cdk kinase assay (e.g., histone H1 assay described infra). Agents that induce increased $p57^{KIP2}$ expression may be identified by their ability to increase the amount of $p57^{KIP2}$ inhibitor activity in the treated cell extract in a manner that is dependant on transcription, i.e., the increase in $p57^{KIP2}$ inhibitor activity is prevented when cells are also treated with an inhibitor of transcription (e.g., actinomycin D). In a similar manner, agents that decrease expression of $p57^{KIP2}$ may be identified by their ability to decrease the amount of $p57^{KIP2}$ inhibitor activity in the treated cell extract in a manner that is dependent upon transcription.

The subject invention further provides a method of determining whether a cell sample obtained from a subject possesses an abnormal amount of $p57^{KIP2}$ protein which comprises (a) obtaining a cell sample from the subject, (b) quantitatively determining the amount of $p57^{KIP2}$ protein in the sample so obtained, and (c) comparing the amount of $p57^{KIP2}$ protein so determined with a known standard, so as to thereby determine whether the cell sample obtained from the subject possesses an abnormal amount of $p57^{KIP2}$ protein.

The subject invention further provides a method of determining whether the amount of $p57^{KIP2}$ protein in a cell sample obtained from a subject having a disease is correlative with the disease which comprises determining whether a cell sample obtained from the subject possesses an abnormal amount of $p57^{KIP2}$, an abnormal amount of $p57^{KIP2}$ in the sample indicating that the amount of $p57^{KIP2}$ in the cell sample obtained from the subject having the disease is correlative with the disease.

The subject invention further provides a method of quantitatively determining the specific activity of p57$^{KIP2}$ protein in a sample which comprises quantitatively determining (i) the ability of the p57$^{KIP2}$ in the sample to inhibit the activation of cyclin-Cdk complex and (ii) the total amount of p57$^{KIP2}$ protein in the sample, and dividing the ability of the p57$^{KIP2}$ so determined by the total amount of p57$^{KIP2}$ so determined so as to thereby quantitatively determine the specific activity of p57$^{KIP2}$ in the sample. In an embodiment, the cyclin-Cdk complex is a cyclinE-Cdk2 complex. In another embodiment, the cyclin-Cdk complex is a cyclinA-Cdk2 complex. In a further embodiment, the cyclin-Cdk complex is a cyclinD-Cdk4 complex. In a still further embodiment, the cyclin-Cdk complex is a cyclinD-Cdk5 complex. In a separate embodiment, the cyclin-Cdk complex is a cyclinD-Cdk6 complex.

The subject invention further provides a kit for practicing the methods of the subject invention. In one embodiment, the kit comprises suitable amounts of p57$^{KIP2}$, cyclin and Cdk. The kit may further comprise suitable buffers, and a package insert describing p57$^{KIP2}$ as an inhibitor of cyclin-Cdk complex activity.

The subject invention further provides a method of diagnosing a hyperproliferative disorder in a subject which disorder is associated with the presence of a p57$^{KIP2}$ mutation in the cells of the subject, which comprises determining the presence of a p57$^{KIP2}$ mutation in the cells of the subject, said mutation being associated with a hyperproliferative disorder, so as to thereby diagnose a hyperproliferative disorder in the subject.

As used herein, "diagnosing" means determining the presence of a hyperproliferative disorder in a subject. In one embodiment, "diagnosing" additionally means determining the type of hyperproliferative disorder in a subject.

As used herein, a "p57$^{KIP2}$ mutation" may be any abnormality in the primary sequence of p57$^{KIP2}$ resulting from an abnormality in the genomic DNA sequence encoding same or controlling the expression of same. For example, the p57$^{KIP2}$ mutation may be a point mutation, a deletion mutation of a portion of p57$^{KIP2}$, or an absence of the entire p57$^{KIP2}$ resulting from an abnormality in the structural gene encoding same or regulatory DNA sequence controlling the expression of same.

Determining the presence of a p57$^{KIP2}$ mutation may be accomplished according to methods well known to those skilled in the art. Such methods include probing a subject's DNA or RNA with a p57$^{KIP2}$ nucleic acid probe. Such methods also include analyzing a protein sample from the subject for p57$^{KIP2}$ structural abnormalities or functional abnormalities resulting therefrom.

In the preferred embodiment, the subject is a human and the hyperproliferative disorder is cancer.

The subject invention further provides a pharmaceutical composition which comprises an effective amount of a recombinant virus capable of infecting a suitable host cell, said recombinant virus comprising the nucleic acid molecule of the subject invention, and a pharmaceutically acceptable carrier.

The "suitable host cell" is any cell in which p57$^{KIP2}$ would normally be produced in a healthy subject.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

Finally, this invention provides a method for treating a subject suffering from a hyperproliferative disorder associated with the presence of a p57$^{KIP2}$ mutation in the cells of the subject, which comprises administering to the subject an amount of the pharmaceutical composition of the subject invention effective to treat the subject.

In the preferred embodiment, the subject is a human and the hyperproliferative disorder is cancer.

In order to facilitate an understanding of the Experimental Details section which follows, certain frequently occurring methods and/or terms are described in Sambrook, et al. (1989).

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods
cDNA cloning and genomic DNA amplification

A lEXlox mouse embryonic cDNA library (Novagen) was screened at low stringency (2×SSC, 0.2% SDS, 25° C.) with a mouse p21 cDNA probe generated by PCR based on the published sequence (El-Deiry et al. 1994). Three positive clones were isolated and sequenced. Two of these clones had deletions in the 5' end when compared to the third one. Two primers (5'GAGGCCAAGCGTTTCATC3' (Seq. ID No. 1) and 5'CAGGAGCCGTTCATCACC3' (Seq. ID No. 2)) were designed to amplify by PCR the genomic DNA sequence encompassing the region missing in the smaller cDNA clones. The resulting amplification product was subcloned into pbluescript (Stratagene®) and sequenced.

In vitro transcription and translation

A blunt ended EcoRI-HindIII fragment containing the coding region of the mouse p57$^{KIP2}$ cDNA with or without an influenza virus hemagglutinin HA epitope (Meloche et al. 1992) tagged at the C-terminus was subcloned into pET21b (Novagen). These constructs were transcribed in vitro using a commercial kit (Promega®) and following the manufacturer's instructions. In vitro translations were performed using Red Nova lysate and accompanying protocol (Novagen). Samples were precipitated with mouse monoclonal anti-HA antibody (Boehringer) as previously described (Wrana et al. 1992).

Recombinant p57$^{KIP2}$ and p27$^{KIP1}$

A PCR-generated fragment of the mouse full length KIP2 cDNA containing the coding region free of mutations was subloned into the T7 overexpression vector pET21a (Novagen). This construct encodes p57$^{KIP2}$ with a flag epitope (Hopp et al. 1988) at the N-terminus. The protein was expressed in BL21(DE3) pLysS bacteria induced with IPTG. Cells were lysed by sonication in a solution containing 50 mM Tris-HCl (pH 7.4), 500 mM sodium chloride, and 20% glycerol. The lysate was clarified by centrifugation and bound to anti-flag M2 beads (IBI) for 1 h at 4° C. Recombinant KIP2 was eluted from the beads with 0.2 mg/ml of flag peptide in a buffer containing 150 mM KCl, 50 mM Tris (pH 7.4), 1 mM EDTA, and 20% glycerol. The eluate was aliquoted and stored at −80° C. Recombinant KIP1 protein was prepared as previously described (Polyak et al. 1994b). Cell transfection, metabolic labeling and immunoprecipitation Subclone R-1B/L17 of the Mv1Lu mink lung epithelial cell line (Attisano et al. 1993; Boyd and Massagué 1989) was routinely cultured in MEM supplemented with 10% fetal bovine serum. Cells were transfected with empty pCMV5 vector (Andersson et al. 1989) or this vector encoding p57, p27 or their indicated epitope-tagged derivatives, using the DEAE-dextran transfection method as previously described (Attisano et al. 1993).

For metabolic labeling experiments, cells were transfected with pCMV5 vector alone or encoding flag-p57, a construct encoding $p57^{KIP2}$ tagged at the N-terminus with the flag epitope. 48 h post-transfection, cells were incubated for 30 min in methionine-free medium supplemented with 10% dialyzed fetal bovine serum, followed by incubation in the same medium for 2 h with 50 µCi/ml of $^{35}$S-methionine (Trans $^{35}$S-label, ICN). Cell pellets were lysed by gentle agitation for 30 minutes at 4° C. in lysis buffer (50 mM Tris HCl, pH 7.4, 200 mM NaCl, 2 mM EDTA, 0.5% NP40, 0.3 mM Na-orthovanadate, 50 mM NaF, 80 µM b-glycerophosphate, 20 mM Na pyrophosphate, 0.5 mM DTT and protease inhibitors). Lysates were clarified by centrifugation (10,000×g for 15 minutes at 4° C.) and immunoprecipitated with flag antibody M2 (IBI).

For protein immunoblotting experiments, cells were transfected with flag-p57. 48 h post-transfection, cells were lysed, the lysates clarifies and precipitated with flag antibody (IBI) in NETN buffer (50 mM NaCl, 50 mM Tris, pH 7.4, 1 mM EDTA, 0.5% NP40). The immunoprecipitates were washed four times in NP40 RIPA buffer, resolved on SDS-PAGE, and electroblotted onto nitrocellulose, and the blots probed with cyclin E antibody (gift of J. Roberts), cyclin A antibody (UBI), cyclin D1 antibody (UBI), cdk2 antibody (UBI) or cdk4 antibody (Pharmingen).

Immunofluorescence analysis

R-1B/L17 cells or COS-1 cells were seeded at a density of 7×10$^5$ cells per 100 mm dish. Two days later the monolayers were transiently transfected with pCMV5 vector alone or with p57-HA vector or flag-p57 vector as indicated. 24 h post-transfection, 25×10$^4$ transfected cells were seeded into a single-well tissue culture chamber slides (Nunc). 24 h later, cells were washed three times with PBS, fixed for 30 min in ice-cold methanol at 4° C., rinsed once with PBS containing 1% Triton X-100, washed three times with PBS, and then incubated for 30 min at room temperature with 1 µg/ml of anti-HA or anti-flag antibody diluted in PBS containing 3% BSA. Cells were then washed four times with PBS and subsequently incubated with 15 µg/ml donkey anti mouse rhodamine-conjugated or fluorescein-conjugated second antibody (Jackson ImmunoResearch Laboratories) diluted in PBS/3% BSA. Cells were then washed four times with PBS, incubated for 5 min at room temperature with 0.1 µg/ml of DAPI (Sigma), washed four times in PBS, and mounted in a solution containing 60% toluene (Cytoseal). Cells were examined by a Zeiss microscope and the images recorded on Kodak Ektachrome 400.

DNA replication and flow cytometry assays

R-1B/L17 cells were transfected with mouse $p27^{KIP1}$ vector, $p57^{KIP2}$ vector or empty pCMV5 vector, and $^{125}$I-deoxyuridine incorporation assays were conducted 48 h after transfection as previously described (Laiho et al. 1990). For flow cytometry assays, cells were transfected with the indicated vectors together with a CD16 vector. 48 h after transfection, cells were stained with anti-CD16 (Wirthmueller et al. 1992), positive cells sorted, and their DNA content analyzed by flow cytometry, all as previously described (Polyak et al. 1994b).

Kinase assays

Baculovirus vectors encoding cyclin A, cyclin B, cyclin E, cyclin D2, cdk2-HA, cdk4-HA and Cdc2-HA (obtained from C. Sherr, J. Roberts or H. Piwnica-Worms) were used to infect insect H5 cells, and cell lysates were prepared as previously described (Desai et al. 1992). Cell extracts containing baculovirally coexpressed cyclins and cdks were incubated with recombinant $p27^{KIP1}$ or $p57^{KIP2}$ at 37° C. for 30 min, precipitated with HA antibody, and the precipitates assayed for histone H1 kinase activity (Koff et al. 1993) or Rb kinase activity (Matsushime et al. 1992) as previously described. The level of phosphorylation of the histone H1 and Rb bands were quantitated using Phosphorimager ImageQuant software (Molecular Dynamics).

Northern blots

A blot containing poly(A)$^+$ RNA from various human tissues (Clontech) and previously hybridized with the mouse $p27^{KIP1}$ cDNA (Polyak et al., 1994b) was stripped in heated water containing 0.5% SDS and reprobed with mouse $p57^{KIP2}$ cDNA probe labeled by the random priming method. Hybridization was done in a solution containing 1% SDS, 10% dextran sulfate, 0.1 mg/ml sonicated salmon sperm DNA, 1M NaCl, and washed in 0.2×SSC, 1% SDS at 65° C. for 30 min. A blot containing equivalent amounts of total RNA from human rhabdomyosarcoma cell lines RH18 and RH30 (provided by R. Benezra, Memorial Sloan-Kettering Cancer Center) was probed with mouse $p57^{KIP2}$ cDNA.

EXPERIMENTAL RESULTS

Cloning of $p57^{KIP2}$

To identify new members of the $p21^{CIP1}/p27^{KIP1}$ family, applicants screened a mouse embryo cDNA library with a mouse p21 cDNA probe. Restriction analysis of positive cDNA clones from this screening showed that three of them corresponded to a species distinct from p21 and p27. Sequence analysis of one of these clones revealed an open reading frame (FIG. 2A) whose first codon (see FIG. 4) is in an optimal context for translation initiation (Kozak 1986). The nucleotide sequence of this open reading frame predicts a product of 348 amino acids with significant sequence similarity to p21 and p27 (FIG. 2A). Most of the similarity is concentrated in a 57-amino acid domain (residues 30–86) in the N-terminal region. The corresponding regions in p21 and p27 also show the highest concentration of sequence similarity between these two proteins (Polyak et al. 1994b; Toyoshima and Hunter 1994). When expressed as a recombinant peptide, the corresponding domain from p27 has CDK inhibitory activity (Polyak et al. 1994b), thus defining structurally and functionally this CDI family.

In the newly cloned species, the CDK inhibitory domain is followed by a proline rich-domain, a highly acidic domain, and a C-terminal domain related to p27 (FIGS. 2A,B). The proline-rich domain is a 82-amino acid segment that starts at residue 108 and is 28% proline. This domain contains a consensus MAP kinase phosphorylation site (FIG. 2A). The acidic domain is a 107-amino acid segment that starts at residue 178 and has a 37% glutamic/aspartic acid content. Many of the glutamic residues are found in 19 contiguous repeats of the consensus tetrad sequences Glu- Pro-Val-Glu (Seq. ID No. 3) and Glu-Gln-X-X (Seq. ID No. 4) (FIG. 2A). The C-terminal domain contains a putative nuclear localization signal and a consensus CDK phosphorylation site, both conserved in p27 together with adjacent sequences (FIGS. 2A and B). Thus, the newly cloned species is characterized by a mosaic structure with four distinct domains and a high content in proline and acidic residues (calculated pI=4.03).

Transcription and translation of this cDNA in vitro yielded a product that migrated with an apparent molecular mass of 57 kD on SDS electrophoresis gels (FIG. 3). Calculation of this value was based on the migration of coelectrophoresed molecular weight markers and computation with ImageQuant software. To address the discrepancy between this value and a calculated molecular mass of 37.3 kD for the entire open reading frame, applicants engineered a construct encoding this protein with an influenza virus hemagglutinin HA epitope (Meloche et al. 1992) linked to the C-terminal arginine. When translated in vitro, this construct yielded a specifically immunoprecipitable product migrating at 57 kD on SDS electrophoresis gels (FIG. 3), confirming the value obtained with the unmodified product. Products of the same size were obtained by transfection of mammalian cells with flag-p57 (see FIG. 6A), a p57 construct tagged at the N-terminus with the flag epitope (Hopp et al. 1988), or by in vitro translation of flag-p57 (data not shown). Applicants therefore refer to this gene product as p57$^{KIP2}$ following the nomenclature that designates p27$^{KIP1}$ and p21$^{CIP1}$, both of which also migrate larger than predicted on SDS electrophoresis gels.

Alternative splicing generates N-terminus heterogeneity

Sequence analysis showed that the two other mouse cDNAs isolated in applicants' screen correspond to p57 mRNA forms lacking 38 and 41 bases, respectively, at the 5' region including the first translation initiator codon (FIG. 4). In both cDNAs, a potential translation initiator codon is located 13 codons downstream of the p57 translation start site, predicting a 335-amino acid product that applicants refer to as p57$^{KIP2}$B PCR amplification of mouse genomic DNA with primers flanking the missing sequence in these cDNAs yielded products that were approximately 200 bp longer than expected from an intronless genomic sequence. Sequence analysis of the amplified product showed the presence of an intervening sequence flanked by consensus splice sites, suggesting that the three different p57 cDNAs correspond to mRNAs generated by splicing of the same intron with differential use of 3' splice acceptor sites (FIG. 4).

Nuclear localization

Given the potential antiproliferative activity of p57 in mammalian cells, applicants studied its expression and activity by transient transfection into the mink lung epithelial cell line R-1B/L17 under conditions that allow >50% of these cells to take up transfected DNA (Attisano et al. 1993; Wrana et al. 1994). Anti-HA immunostaining of cultures expressing a transfected p57-HA demonstrated specific localization of this product in the nucleus with no specific staining discernable in other cellular compartments (FIGS. 5A–D). When transfected into the same cells, a version of this construct truncated at the C-terminal end of the acidic domain (amino acid 281) was expressed in the cytoplasm and excluded from the nucleus (data not shown), suggesting that nuclear localization is specified by the putative nuclear localization signal in the missing domain (FIG. 2). Nuclear localization of p57 was confirmed by anti-Flag immunostaining of monkey COS-1 cells overexpressing a transfected flag-p57 construct (FIGS. 5E–H). Examination of the entire stained field suggested that the enlarged morphology of some of the COS-1 nuclei (see FIG. 5F) was not a specific effect of p57 but an effect of cell transfection with the pCMV5 vector used.

Cdk interaction in vivo and cdk inhibitory activity in vitro

To identify cellular proteins that interact with p57 in vivo, flag-p57 transfected cells were metabolically labeled with $^{35}$S-methionine and cell lysates precipitated with flag antibody. This precipitation yielded flag-p57 and various specifically coprecipitating products, as determined by SDS-PAGE (FIG. 6A). To determine whether these products included cyclin-dependent kinase components, gels containing anti-flag precipitates from unlabeled cells were subjected to immunoblotting with various cyclin and cdk antibodies. The results of these assays demonstrated that p57 specifically coprecipitated with cdk2, cdk4, and cyclins E, A and D1 (FIG. 6B).

Figure 7A:
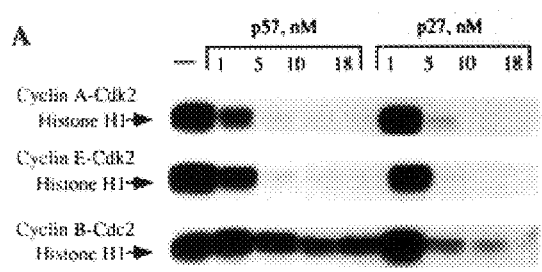
Figure 7B:
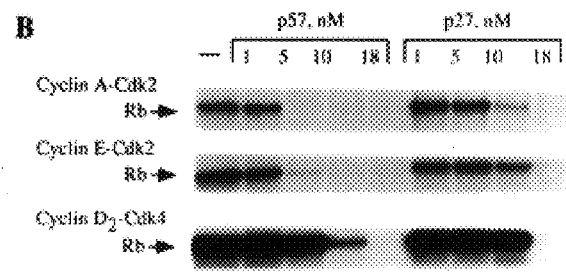

To confirm the ability of p57 to interact with cyclin-cdk complexes and affect their kinase activity, applicants purified bacterially-produced flag-tagged p57 by affinity chromatography on anti-flag beads, added this product to recombinant cyclin-cdk preparations, and assayed their kinase activity. p57 was able to completely inhibit the H1 kinase activity of cyclin E-cdk2 and cyclin A-cdk2, and was 10-fold more potent against these G1 CDKs than against the mitotic CDK cyclin B1-Cdc2 (FIGS. 7A, C). Using histone H1 as a substrate, half-maximal inhibition of cyclin E-cdk2 and cyclin A-cdk2 was observed with 0.5 nM p57 (FIGS. 7A, C). A similar kinase inhibition pattern was observed using Rb as the substrate for cyclin E-cdk2, cyclin A-cdk2 or cyclin D2-cdk4. When tested in parallel against G$_1$ CDKs, p57 was reproducibly two- to five-fold more potent than mouse p27 (FIGS. 7B, C). In contrast, p57 was less potent than p27 as an inhibitor of cyclin B1-Cdc2 (FIGS. 7A, C).

Inhibition of cell entry into S phase

Since p57 was able to interact with CDK components in intact cells and inhibited CDKs in vitro, applicants tested its ability to inhibit cell cycle progression. For this purpose, a p57 expression vector was transiently transfected into R-1B/L17 cells, and the transfectants analyzed 48 hours later. As determined by measuring $^{125}$I-deoxyuridine incorporation, the relative rate of DNA synthesis at this time was markedly reduced compared to controls transfected with vector alone (FIG. 8). This effect was similar to that caused by transfection of p27 (FIG. 8).

To determine at what point of the cycle these cells were arrested, p57 was cotransfected with the cell surface marker CD16 (Wirthmueller et al. 1992). 48 hours after transfection, cells were stained with anti-CD16, sorted, and the CD16$^+$ population was subjected to flow cytometry to determine its cell cycle distribution based on DNA content. This analysis demonstrated a striking accumulation of p57 transfected cells in G1 phase at the expense of both S phase and G2/M phase (FIG. 8). These results suggest that p57 arrests the cell cycle in G1 phase.

mRNA expression pattern in human tissues

Figure 9:
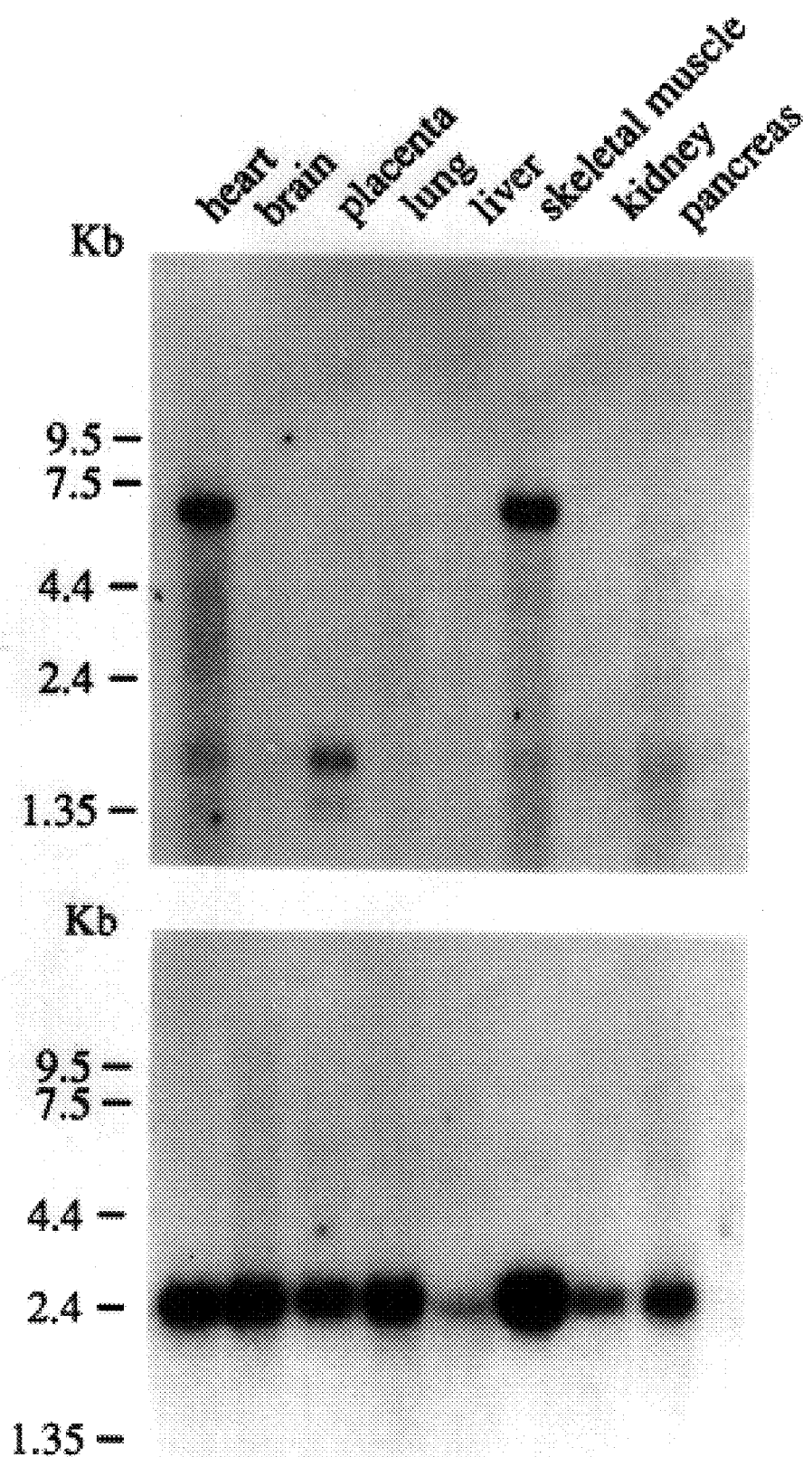

Northern blot assays with a mouse p57 cDNA probe used at high stringency showed the presence of hybridizing RNA species of 1.5 kb and 7 kb in a limited subset of human tissues (FIG. 9). This is in contrast to the presence of a single p27 mRNA in all these tissues as determined by probing of the same blot with a p27 probe (FIG. 9; Polyak et al. 1994b). The 1.5 kb p57 mRNA species was present at relatively high levels in placenta, at low levels in skeletal muscle, heart, kidney and pancreas, was detectable in brain only after prolonged autoradiographic exposure of the blot, and was not detectable in lung or liver. Among the tissues tested, the 7 kb species was detectable only in skeletal muscle and heart (FIG. 9), and in two human rhabdomyosarcoma cell lines (data not shown). The relationship between these two mRNA species and the basis for their marked size difference remain to be determined.

EXPERIMENTAL DISCUSSION

Applicants have identified p57$^{KIP2}$, a new member of the KIP/CIP family of CDK inhibitors that has biochemical and biological activities consistent with a role in negative regulation of G1 phase in the cell cycle. p57 is distinguished from p21 and p27 by its unique domain structure and distinct tissue distribution pattern. The properties of this novel CDI are indicative of a high degree of diversity in this family of inhibitors.

p57$^{KIP2}$ domain structure

The longest p57 open reading frame predicts a 348 amino-acid protein with a calculated mass of 37.3 kD. However, the products translated from this cDNA in vitro, in E. coli and in mammalian cells migrate on SDS electrophoresis gels as 57 kD proteins. Applicants have confirmed the authenticity of these products by immunoprecipitating recombinant p57 derivatives epitope-tagged at the N-terminus or the C-terminus. The anomalous migration of p57 on SDS gels might result from a rigid, elongated shape caused by the high number of prolines in this molecule. p21 and p27 also run anomalously slow on SDS gels, their respective 21 kD and 27 kD values being larger than their theoretical molecular masses (Harper et al. 1993; Polyak et al. 1994b). Accordingly, applicants named p57$^{KIP2}$ after its apparent size on SDS gels and also to denote a higher degree of sequence similarity between p57$^{KIP2}$ and p27$^{KIP1}$ than between p57$^{KIP2}$ and p21$^{CIP1}$ (see below).

Three distinct p57 cDNAs that differ at the start of their open reading frames were cloned from a mouse embryo cDNA library. The two smaller cDNAs are missing 38 and 41 bases, respectively, that are present in the larger clone. PCR amplification of mouse genomic DNA with primers that flank the deleted sequences amplified a product consistent with the presence of a ~0.2 kb intron in this region of the gene. Sequence analysis of the amplified product reveals that the three cDNAs correspond to messages generated by the use of distinct splice acceptor sites. The first acceptor site lies 9 bp upstream of the first methionine codon, which is in an optimal context for translation initiation. Use of the other two splice acceptor sites deletes this codon and additional coding region, yielding two nearly identical messages whose first possible translation initiator would yield in both cases a product 13 amino acids shorter than p57 at the N-terminus. Applicants refer to this product as p57$^{KIP2B}$, or p57B, but have not tested it in inhibition assays or confirmed that it is actually expressed in the cell.

Following this heterogeneous N-terminal region, the predicted p57 protein sequence has four distinct domains including, in order, a p21/p27-related CDK inhibitory domain, a proline-rich domain, an acidic domain and a C-terminal nuclear targeting domain. The CDK inhibitory domain is a 57-amino acid region (residues 30–86) that contains most of the sequence similarity to p21 (36% identity) and p27 (47% identity). The corresponding regions in p21 and p27 also contain most of the sequence similarity (44% identity) between these two proteins (Polyak et al. 1994b; Toyoshima and Hunter 1994). The CDK binding and inhibitory activities of p27 segregate with this region, which retains these activities when produced as a recombinant peptide (Polyak et al. 1994b). Therefore, applicants infer that the corresponding domains in p21 and p57 contain the CDK inhibitory activity of these proteins. The identification of p57 helps establish this domain as the structural motif defining this CDI family.

The entire p57 portion following the CDK inhibitory domain has a relatively high proline content. However, a 82-amino acid region extending from residue 108 is particularly proline-rich (28% proline). This domain contains a MAP kinase consensus phosphorylation site. Although applicants have no evidence that this site is used in vivo, it is worth noting that the CDK inhibitor Far1 from Saccharomyces cerevisiae is phosphorylated by MAP kinases in response to cell stimulation by mating pheromone, this phosphorylation being required for Far1 activation (Peter et al. 1993; Peter and Herskowitz 1994). The p57 proline-rich domain overlaps with an acidic domain that extends from residues 178–284 and is 37% glutamic or aspartic acid. Besides conferring a strongly acidic character to the entire molecule (calculated pI=4.03), this region is unusual in that its glutamic residues are arranged in 19 contiguous repeats of the tetrapeptide consensus sequences Glu-Pro-Val-Glu (Seq. ID No. 3) and Glu-Gln-X-X (Seq. ID No. 4). A search of published sequence databases did not turn up any other protein with a similar repetitive motif. No equivalent proline-rich or acidic domains are present in p21 or p27. The presence of these domains in p57, which account for its size difference with p21 and p27, may confer the ability to establish specific protein-protein interactions affecting the localization or CDI function of p57 in vivo. Alternatively, these domains could have functions entirely separate from the CDI function. A precedent for the multifunctional nature of these molecules is provided by p21 which has PCNA-dependent DNA polymerase d inhibitory activity (Flores-Rozas et al. 1994; Waga et al. 1994).

The C-terminal domain of p57 that follows the proline-rich and acidic domains shows sequence similarity to p27. The similarity is clear in two motifs, a putative nuclear localization signal (NLS) and a CDK consensus phosphorylation site. p27 contains a putative bipartite NLS (Polyak et al. 1994b; Toyoshima and Hunter 1994) characterized by two short clusters of basic residues separated by 10 residues (Dingwall and Laskey 1991). The putative NLS in p57 is limited to a KRKR (Seq. ID No. 12) sequence (Boulikas 1993), but its relative position in the molecule and downstream sequence are similar to those of the NLS in p27. Immunostaining of cells transfected with epitope-tagged p57 demonstrated that this protein localizes to the nucleus. Furthermore, a p57 construct missing the C-terminal domain was localized in the cytoplasm and excluded from the nucleus, suggesting that the putative NLS in p57 is functional. The location and adjacent sequence of a consensus CDK phosphorylation site near the C-terminus of p57 are conserved in p27 but not found in p21. These sites might be involved in feed-back regulation of p57 and p27 by their target CDKs.

Functional properties and expression pattern of p57$^{KIP2}$

When purified as a recombinant protein from bacteria and added to kinase assays of recombinant CDK preparations, p57 acts as a potent inhibitor of the $G_1$ CDKs cyclin E-cdk2 and cyclin D2-cdk4 and the S phase CDK cyclin A-cdk2. p57 inhibits both Rb and histone H1 phosphorylation by these kinases, and in all our experiments its potency was several-fold higher than that of recombinant p27 produced and assayed in parallel with p57. However, p57 was less potent than p27 as an inhibitor of cyclin B-Cdc2. Preincubation of recombinant CAK (cyclin H-cdk7/MO15 complex; Fisher and Morgan 1994) with p57 did not inhibit the CAK activity of these complexes (J. Y. Kato, C. Sherr and M.-H. L., personal communication).

The in vitro activity of p57 suggests that it may act as a CDI primarily in G1 phase. In support of this possibility, transfection of p57 into Mv1Lu lung epithelial cells induces a profound arrest of the proliferative cycle with accumulation of cells in G1. Immunoprecipitation of p57 from these cells retrieves several specifically coprecipitating proteins. Immunoblot assays using appropriate antibodies show that these proteins include cdk2, cdk4 and cyclins E, D1 and A, all of which are important components of the G1 CDK system. Identification of cell types that express endogenous p57 will be necessary in order to establish the CDK components that are preferentially targeted by p57 in vivo.

The expression pattern of p57 mRNA in various adult human tissues suggests that its distribution is more restricted than that of p21 and p27, both of which are expressed in most tissues examined (Harper et al. 1993; Polyak et al. 1994b). Two human mRNA species of 1.5 kb and 7 kb, respectively, hybridize with the mouse p57 probe under relatively high stringency conditions. The basis for the size difference between these two messages remains to be determined, but may result from differential processing of the p57 transcript or from the existence of different p57-related genes. The 7 kb mRNA is detectable only in skeletal muscle and heart among the tissues that applicants tested, and in human rhabdomyosarcoma cells. The 1.5 kb species is present in placenta and at low levels in muscle, heart, brain, kidney and pancreas, and was not detected in lung or liver. Some of these tissues are highly heterogeneous in cellular composition, and their low p57 mRNA levels may reflect expression in only certain cell types.

The present results identify p57 as a putative regulator of G1 phase. In view of its restricted expression pattern, p57 may function in only certain tissues or cell types. Furthermore, the function of p57 in these tissues may be unique as a result of the unusual protein domains present in this inhibitor. The availability of its cDNA should allow a further exploration of these questions.

REFERENCES

Andersson, S, Davis, D. N., Dahlback, H., Jornvall, H., and Russell, D. W. 1989. Cloning, structure and expression of the mitochondrial cytochome P-450 sterol 26-hydroxylase, a bile acid biosynthetic enzyme. *J. Biol. Chem.* 264: 8222–8229.

Attisano, L., Cárcamo, J., Ventura, F., Weis, F. M. B., Massagué, J., and Wrana, J. L. 1993. Identification of human activin and TGF-b type I receptors that form heteromeric kinase complexes with type II receptors. *Cell* 75: 671–680.

Boulikas, T. 1993. Nuclear localization signals (NLS). *Crit. Revs. Eukar. Gene Expr.* 3: 193–227.

Boyd, F. T. and Massagué, J. 1989. Growth inhibitory response to transforming growth factor-b linked to expression of a 53 kDa cell surface TGF-b receptor. *J. Biol. Chem.* 274: 2272–2278.

Caldas, C., Hahn, S. A., da Costa, L. T., Redston, M. S., Schutte, M., Seymour, A. B., Weinstein, C. L., Hruban, R. H., Yeo, C. J., and Kern, S. E. 1994. Frequent somatic mutations and homozygous deletions of the p16 (MTS1) gene in pancreatic adenocarcinoma. *Nature Genet.* 8: 27–32.

Cocks, B. G., Vairo, G., Bodrug., S. E., and Hamilton, J. A. 1992. Supression of growth factor-induced CYL-1 cyclin gene expression by antiproliferative agents. *J. Biol. Chem.* 267: 12307–12310.

Desai, D., Gu, Y., and Morgan, D. O. 1992. Activation of human cyclin-dependent kinases in vitro. *Mol. Biol. Cell* 3: 571–582.

Dingwall, C. and Laskey, R. A. 1991. Nuclear targeting sequences: a consensus? *Trends. Biochem. Sci.* 16: 478–481.

El-Deiry, W. S., Harper, J. W., O'Connor, P. M., Velculescu, V. E., Canman, C. E., Jackman, J., Pietenpol, J. A., Burrell, M., Hill, D. E., Wang, Y., Wiman, K. G., Mercer, W. E., Kastan, M. B., Kohn, K. W., Elledge, S. J., Kinzler, K. W., and Vogelstein, B. 1994. WAF1/CIP1 is induced in p53-mediated G1 arrest and apoptosis. *Cancer Res.* 54: 1169–1174.

El-Deiry, W. S., Tokino, T., Velculescu, V. E., Levy, D. B., Parsons, R., Trent, J. M., Lin, D., Mercer, E., Kinzler, K. W., and Vogelstein, B. 1993. WAF1, a potential mediator of p53 tumor suppression. *Cell* 75: 817–825.

Ewen, M. E., Sluss, H. K., Whitehouse, L. L., and Livingston, D. M. 1993. TGFb inhibition of Cdk4 synthesis is linked to cell cycle arrest. *Cell* 74: 1009–1020.

Fisher, R. P. and Morgan, D. O. 1994. A novel cyclin associates with MO15/CDK7 to form the CDK-activating kinase. *Cell* 78: 713–724.

Fisher, R. P. and D. O. Morgan, 1994, A novel cyclin associates with MO15/CDK7 to form the CDK-activating kinase. *Cell,* 78:713–724.

Flores-Rozas, H., Kelman, Z., Dean, F. B., Pan, Z-Q., Harper, J. W., Elledge, S. J., O'Donnel, M., and Hurwitz, J. 1994. Cdk-interacting protein 1 directly binds with proliferating cell nuclear antigen and inhibits DNA replication catalyzed by the DNA polymerase d holoenzyme. *Proc. Natl. Acad. Sci. USA* 91: 8655–8659.

Geng, Y. and Weinberg, R. A. 1993. Transforming growth factor b effects on expression of G1 cyclins and cyclin-dependent protein kinases. *Proc. Natl. Acad. Sci. U.S.A.* 90: 10315–10319.

Gu, Y., Turck, C. W., and Morgan, D. O. 1993. Inhibition of CDK2 activity in vivo by an associated 20K regulatory subunit. *Nature* 366: 707–710.

Guan, K.-L., Jenkins, C. W., Li, Y., Nichols, M. A., Wu, X., O'Keefe, C. L., Matera, A. G., and Xiong, Y. 1994. Growth suppression by p18, a $p16^{INK4/MTS1}$ and $p14^{INK4/MTS2}$-related CDK6 inhibitor, correlates with wild-type pRb function. *Genes Dev.* 8: 2939–2952.

Hannon, G. J. and Beach, D. 1994. $p15^{INK4B}$ is a potential effector of TGF-b-induced cell cycle arrest. *Nature* 371: 257–261.

Harper, J. W., Adami, G. R., Wei, N., Keyomarsi, K., and Elledge, S. J. 1993. The p21 cdk-interacting protein Cip1 is a potent inhibitor of G1 cyclin-dependent kinases. *Cell* 75: 805–816.

Hinds, P. and Weinberg, R. A. 1994. Tumor suppressor genes. *Curr. Opin. Gent. Dev.* 4: 135–141.

Hopp, T. P., Prickett, K. S., Price, V. L., Libby, R. T., March, C. J., Cerretti, D. P., Urdal, D. L., and Conlon, P. J. 1988. A short polypeptide marker sequence useful for recombinant protein identification and purification. *Bio/Technology* 6: 1204–1210.

Hunter, T. and Pines, J. 1994. Cylins and cancer II: cyclin D and CDK inhibitiors come of age. *Cell* 79: 573–582.

Huppi, K., Siwarski, D., Dosik, J., Chedid, M., Reed, S., Mock, B., Givol, D., and Mushinski, J. F. 1994. Molecular cloning, sequencing, chromosomal localization and expression of mouse p21 (Waf1). *Oncogene* 9: 3017–3020.

Kamb, A., Gruis, N. A., Weaver-Feldhaus, J., Liu, Q., Harshman, K., Tavtigian, S. V., Stockert, E., Day III, R. S., Johnson, B. E., and Skolnick, M. H. 1994. A cell cycle regulator potentially involved in genesis of many tumor types. *Science* 264: 436–440.

Kamb, A., N. A., Gruis, J., Weaver-Feldhaus, Q., Liu, K., Harshman, S. V., Tavtigian, E., Stockert, R. S., Day III, B. E., Johnson, and M. H. Skolnick, 1994, A cell cycle regulator potentially involved in genesis of many tumor types. *Science,* 264:436–440.

Kato, J., Matsuoka, M., Polyak, K., Massagué, J., and Sherr, C. J. 1994. Cyclic AMP-induced G1 phase arrest mediated by an inhibitor (p27$^{KIP1}$) of cyclin-dependent kinase-4 activation. *Cell* 79: 487–496.

Koff, A., Ohtsuki, M., Polyak, K., Roberts, J. M., and Massagué, J. 1993. Negative regulation of G1 in mammalian cells:inhibition of cyclin E-dependent kinase by TGF-b. *Science* 260: 536–539.

Kozak, M. 1986. Point mutations define a sequence flanking the AUG initiator codon that modulates translation by eukaryotic ribosomes. *Cell* 44: 283–292.

Laiho, M., DeCaprio, J. A., Ludlow, J. W., Livingston, D. M., and Massagué, J. 1990. Growth inhibition by TGF-b1 linked to suppression of retinoblastoma protein phosphorylation. *Cell* 62: 175–185.

Li, Y., Jenkins, C. W., Nichols, M. A., and Xiong, Y. 1994a. Cell cycle expression and p53 regulation of the cyclin-dependent kinase inhibitor p21. *Oncogene* 9: 2261–2268.

Li, Y., Nichols, M. A., Shay, J. W., and Xiong, Y. 1994b. Transcriptional repression of the D-type cyclin-dependent kinase inhibitor p16 by the retinoblastoma susceptibility gene product pRb. *Cancer Res.* 54: 6078–6082.

Matsushime, H., Ewen, M. E., Strom, D. K., Kato, J.-Y., Hanks, S. K., Roussel, M. F., and Sherr, C. J. 1992. Identification and properties of an atypical catalytic subunit (p34$^{PSK-J3/cdk4}$) for mammalian D type G1 cyclins. *Cell* 71: 323–334.

Matsushime, H., Roussel, M. F., Ashnun, R. A., and Sherr, C. J. 1991. Colony-stimulation factor 1 regulates novel cyclins during the G1 phase of the cell cycle. *Cell* 65: 701–713.

Meloche, S., Pages, G., and Pouyssegur, J. 1992. Functional expression and growth factor activation of an epitope tagged p44 mitogen activated protein kinase, p44$^{mapk}$. *Mol. Biol. Cell.* 3: 63–71.

Mori, T., Miura, K., Aoki, T., Nishihara, T., Mori, S., and Nakamura, M. 1994. Frequent somatic mutation of MTS1/CDK4I gene in esophageal squamous cell carcinoma. *Cancer Res.* 54: 3396–3397.

Noda, A., Ning, Y., Venable, S. F., Pereira-Smith, O. M., and Smith, J. R. 1994. Cloning of senescent cell-derived inhibitors of DNA synthesis using an expression screen. *Exp. Cell Res.* 211: 90–98.

Nourse, J., Firpo, E., Flanagan, M. W., Meyerson, M., Polyak, K., Lee, M-H., Massagué, J., Crabtree, G. R., and Roberts, J. M. 1994. Rapamycin prevents IL-2-mediated elimination of the cyclin-CDK kinase inhibitor, p27KIP1. *Nature* 372: 570–573.

Peter, M., Gartner, A., Horecka, J., Ammerer, G., and Herskowitz, I. 1993. FAR1 links the signal transduction pathway to the cell cycle machinery in yeast. *Cell* 73: 747–760.

Peter, M. and Herskowitz, I. 1994. Direct inhibition of the yeast cyclin-dependent kinase Cdc28-Cln by Far1. *Science* 265: 1228–1231.

Polyak, K., Kato, J.-Y., Solomon, M. J., Sherr, C. J., Massagué, J., Roberts, J. M., and Koff, A. 1994a. p27$^{KIP1}$, a cyclin-Cdk inhibitor, links transforming growth factor-b and contact inhibition to cell cycle arrest. *Genes Dev* 8: 9–22.

Polyak, K., Lee, M-H., Erdjument-Bromage, H., Koff, A., Tempst, P., Roberts, J. M., and Massagué, J. 1994b. Cloning of p27$^{KIP1}$ a cyclin-cdk inhibitor and a potential mediator of extracellular antimitogenic signals. *Cell* 78: 59–66.

Serrano, M., Hannon, G. J., and Beach, D. 1993. A new regulatory motif in cell cycle control causing specific inhibition of cyclin D/CDK4. *Nature* 366: 704–707.

Sherr, C. J. 1994a. G1 phase progression: cycling on cue. *Cell* 79: 551–555.

Sherr, C. J. 1994b. The ins and outs of Rb: coupling gene expression to the cell cycle clock. *Trends Cell Biol.* 4: 15–18.

Toyoshima, H. and Hunter, T. 1994. p27, a novel inhibitor of G1 cyclin-Cdk protein kinase activity, is related to p21. *Cell* 78: 67–74.

Waga, S., Hannon, G. J., Beach, D., and Stillman, B. 1994. The p21 inhibitor of cyclin-dependent kinases controls DNA replication by interaction with PCNA. *Nature* 369: 574–578.

Wirthmueller, U., Kurosaki, T., Murakami, M. S., and Ravetch, J. V. 1992. Signal transduction by FcδRIII (CD16) is mediated through the δ chain. *J. Exp. Med.* 175: 1381–1390.

Wrana, J. L., Attisano, L., Carcamo, J., Zentella, A., Doody, J., Laiho, M., Wang, X.-F., and Massagué, J. 1992. TGF-b signals through a heteromeric protein kinase receptor complex. *Cell* 71: 1003–1014.

Wrana, J. L., Attisano, L., Wieser, R., Ventura, F., and Massague, J. 1994. Mechanism of activation of the TGF-b receptor. *Nature* 370: 341–347.

Xiong, Y., Hannon, G. J., Zhang, H., Casso, D., Kobayashi, R., and Beach, D. 1993. p21 is a universal inhibitor of cyclin kinases. *Nature* 366: 701–704.

Zhang, H., Hannon, G. J., and Beach, D. 1994. p21-containing cyclin kinases exist in both active- and inactive states. *Genes Dev.* 8: 1750–1758.

Genbank Accession Number. The accession number for the mouse p57 nucleotide sequence reported in this specification is U20553.

---

What is claimed is:

1. A plasmid designated as pMH115 (ATCC Accession No. 97100).

2. A plasmid designated as pMH178 (ATCC Accession No. 97101).

3. A purified oligonucleotide comprising a contiguous nucleotide sequence selected from the group consisting of Seq. I.D. No. 11 and Seq. I.D. No. 14.

4. A DNA molecule of claim 3.

5. A cDNA molecule of claim 4.

6. An RNA molecule of claim 3.

7. A vector comprising the nucleic acid molecule of claim 3.

8. A vector of claim 7, wherein the vector is a plasmid.

9. The vector of claim 7, wherein the vector is a virus.

10. A host vector system for the production of a mammalian p57$^{KIP2}$ which comprises the vector of claim 7 in a suitable host.

11. The host vector system of claim 7, wherein the suitable host is a bacterial cell.

12. The host vector system of claim 7, wherein the suitable host is an eucaryotic cell.

13. The host vector system of claim 7, wherein the eucaryotic cell is an insect cell.

14. The host vector system of claim 7, wherein the eucaryotic cell is a mammalian cell.

15. A nucleic acid oligonucleotide comprising a nucleic acid molecule of at least 15 nucleotides capable of specifically hybridizing with a unique sequence included within the sequence of the nucleic acid molecule of claim 3.

16. A DNA oligonucleotide of claim 15.

17. An RNA probe of claim 15.

18. A purified mammalian p57$^{KIP2}$ encoded by the oligonucleotide of claim 3.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 18 base pairs (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GAGGCCAAGC GTTTCATC                                                  18

(2) INFORMATION FOR SEQ ID NO:2:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

CAGGAGCCGT TCATCACC                                                  18

(2) INFORMATION FOR SEQ ID NO:3:

(i) SEQUENCE CHARACTERISTICS:
          (A) LENGTH: 4 amino acids
          (B) TYPE: amino acid
          (C) STRANDEDNESS: Not Relevant
          (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:3:

Glu Pro Val Glu
1

(2) INFORMATION FOR SEQ ID NO:4:

(i) SEQUENCE CHARACTERISTICS:
          (A) LENGTH: 4 amino acids
          (B) TYPE: amino acid
          (C) STRANDEDNESS: Not Relevant
          (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:4:

Glu Gln Xaa Xaa
1

(2) INFORMATION FOR SEQ ID NO:5:

(i) SEQUENCE CHARACTERISTICS:
          (A) LENGTH: 348 amino acids
          (B) TYPE: amino acid (C) STRANDEDNESS: Not Relevant
(D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:5:

```
Met Gly Met Ser Asp Val Tyr Leu Arg Ser Arg Thr Ala Met Glu Arg
1               5                  10                  15

Leu Ala Ser Ser Asp Thr Phe Pro Val Ile Ala Arg Ser Ser Ala Cys
                20                  25                  30

Arg Ser Leu Phe Gly Pro Val Asp His Glu Glu Leu Gly Arg Glu Leu
            35                  40                  45

Arg Met Arg Leu Ala Glu Leu Asn Ala Glu Asp Gln Asn Arg Trp Asp
        50                  55                  60

Phe Asn Phe Gln Gln Asp Val Pro Leu Arg Gly Pro Gly Arg Leu Gln
65                  70                  75                  80

Trp Met Glu Val Asp Ser Glu Ser Val Pro Ala Phe Tyr Arg Glu Thr
                85                  90                  95

Val Gln Val Gly Arg Cys Arg Leu Gln Leu Gly Pro Arg Pro Pro Pro
            100                 105                 110

Val Ala Val Ala Val Ile Pro Arg Ser Gly Pro Pro Ala Gly Glu Ala
        115                 120                 125

Pro Asp Gly Leu Glu Glu Ala Pro Glu Gln Pro Pro Ser Ala Pro Ala
    130                 135                 140

Ser Ala Val Val Ala Asp Ala Thr Pro Ala Thr Pro Ala Pro Ala
145                 150                 155                 160

Ser Asp Leu Thr Ser Asp Pro Ile Pro Glu Val Thr Leu Val Ala Thr
                165                 170                 175

Ser Asp Pro Thr Pro Asp Pro Ile Pro Asp Ala Asn Pro Asp Val Ala
            180                 185                 190

Thr Arg Asp Gly Glu Glu Gln Val Pro Glu Gln Val Ser Glu Gln Gly
        195                 200                 205

Glu Glu Ser Gly Ala Glu Pro Gly Asp Glu Leu Gly Thr Glu Pro Val
    210                 215                 220

Ser Glu Gln Gly Glu Glu Gln Gly Ala Glu Pro Val Glu Glu Lys Asp
225                 230                 235                 240

Glu Glu Pro Glu Glu Glu Gln Gly Ala Glu Pro Val Glu Glu Gln Gly
                245                 250                 255

Ala Glu Pro Val Glu Glu Gln Asn Gly Glu Pro Val Glu Glu Gln Asp
            260                 265                 270

Glu Asn Gln Glu Gln Arg Gly Gln Glu Leu Lys Asp Gln Pro Leu Ser
        275                 280                 285

Gly Ile Pro Gly Arg Pro Ala Pro Gly Thr Ala Ala Ala Asn Ala Asn
    290                 295                 300

Asp Phe Phe Ala Lys Arg Lys Arg Thr Ala Gln Glu Asn Lys Ala Ser
305                 310                 315                 320

Asn Asp Val Pro Pro Gly Cys Pro Ser Pro Asn Val Ala Pro Gly Val
                325                 330                 335

Gly Ala Val Glu Gln Thr Pro Arg Lys Arg Leu Arg
            340                 345
```

(2) INFORMATION FOR SEQ ID NO:6:

```
    (i) SEQUENCE CHARACTERISTICS:
        (A) LENGTH: 197 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:6:

Met Ser Asn Val Arg Val Ser Asn Gly Ser Pro Ser Leu Glu Arg Met
1               5                  10                  15

Asp Ala Arg Gln Ala Asp His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Arg Tyr Glu Trp Gln Glu Val Glu
65                  70                  75                  80

Arg Gly Ser Leu Pro Glu Phe Tyr Tyr Arg Pro Pro Arg Pro Pro Lys
                85                  90                  95

Ser Ala Cys Lys Val Leu Ala Gln Glu Ser Gln Asp Val Ser Gly Ser
            100                 105                 110

Arg Gln Ala Val Pro Leu Ile Gly Ser Gln Ala Asn Ser Glu Asp Arg
        115                 120                 125

His Leu Val Asp Gln Met Pro Asp Ser Ser Asp Asn Gln Ala Gly Leu
    130                 135                 140

Ala Glu Gln Cys Pro Gly Met Arg Lys Arg Pro Ala Ala Glu Asp Ser
145                 150                 155                 160

Ser Ser Gln Asn Lys Arg Ala Asn Arg Thr Glu Glu Asn Val Ser Asp
                165                 170                 175

Gly Ser Pro Asn Ala Gly Ile Val Glu Gln Thr Pro Lys Lys Pro Gly
            180                 185                 190

Leu Arg Arg Gln Thr
            195

(2) INFORMATION FOR SEQ ID NO:7:

(i) SEQUENCE CHARACTERISTICS:
        (A) LENGTH: 159 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:7:

Met Ser Asn Pro Gly Asp Val Arg Pro Val Pro His Arg Ser Lys Val
1               5                  10                  15

Cys Arg Cys Leu Phe Gly Pro Val Asp Ser Glu Gln Leu Arg Arg Asp
            20                  25                  30

Cys Asp Ala Leu Met Ala Gly Cys Leu Gln Glu Ala Arg Glu Arg Trp
        35                  40                  45
```

```
Asn Phe Asp Phe Val Thr Glu Thr Pro Leu Gly Asn Phe Val Trp
    50                  55                  60

Glu Arg Val Arg Ser Leu Gly Leu Pro Lys Val Tyr Leu Ser Pro Gly
65                  70                  75                  80

Ser Arg Ser Arg Asp Asp Leu Gly Gly Asp Lys Arg Pro Ser Thr Ser
                85                  90                  95

Ser Ala Leu Leu Gln Gly Pro Ala Pro Glu Asp His Val Ala Leu Ser
            100                 105                 110

Leu Ser Cys Thr Leu Val Ser Glu Arg Pro Glu Asp Ser Pro Gly Gly
        115                 120                 125

Pro Gly Thr Ser Gln Gly Arg Lys Arg Arg Gln Thr Ser Leu Thr Asp
    130                 135                 140

Phe Tyr His Ser Lys Arg Arg Leu Val Phe Cys Lys Arg Lys Pro
145                 150                 155
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:8:

```
Met Gly Met Ser Asp Val Tyr Leu Arg Ser Arg Thr Ala Met Glu
1               5                   10                  15
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
TCACCAATCA GCCAGGTAGC C                                       21
```

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
GCACAGCCTT CGACCATGGG CATGTCCGAC GTGTACCTCC GCAGCAGAAC AGCGATGGAA    60
```

(2) INFORMATION FOR SEQ ID NO:11:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

```
CGACGGTATC GATAAGCTTG ATATCGAATT CCGGTTTTTT CTTTTTTCTT TTTTTTGCAC      60
TGAGTTTCAG CAGAGATTAA ACATTTTATA TAAATGACTC TTAAAGCTTT ACACCTTGGG     120
ACCAGTGTAC CTTCTCGTGC AGAATACATT TAGATATAAA AAGACGTTAT TAATACATTG     180
CACAGTTTTC AAAATTTAAA AACAAAACCG AACGCTGCTC TGCGGCACGC GCCGCGGTTG     240
CTGCTACATG AACGGTCCCA GCCGAGGCCC AGCGCCCTTC CAACGTCCGC TGCCCCGGCA     300
GGTTCCCTCG GGGCTCTTTG GGCTCTAAAT TGGCTCACCG CAGCCTCTTG CGCGGGGTCT     360
GCTCCACCGA GCCCACGCCA GGGGCGGCGC TTGGAGAGGG ACACGGCGCG GGGACATCGC     420
CCGACGACTT CTCAGGCGCT GATCTCTTGC GCTTGGCGAA GAAATCGGAG ATCAGAGGCC     480
CGGACAGCTT CTTGATCGCC GCGCCGTTGG CGTGGCGGCC GCGGTGCCGG CCGGGGACGT     540
CCCGAAATCC CCGAGTGCAG CTGGTCAGCG AGAGGCTCCT GGCCGCGCTG CCCCTGGTTC     600
GCGCCCTGCT CGGCGCTCTC TTGAGGCGCC GCGTCCGGGG CCGGGGCCGG GGCGGGGGCC     660
GGGGCCGGGG CCGGGGCCGG GGCTGGGGCC GGGGCCGCGA CTGGAGCCGG GGCCGGAGCC     720
GGAGCCGGAG CCGGGGCCGG GCGGGCAGGA CCGCGACGGA CCGAGCGCGA CCGA           774
```

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:12:

Lys Arg Lys Arg
1

(2) INFORMATION FOR SEQ ID NO:13:

(i) SEQUENCE CHARACTERISTICS:
        (A) LENGTH: 348 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:13:

```
Met Gly Met Ser Asp Val Tyr Leu Arg Ser Arg Thr Ala Met Glu Arg
1               5                   10                  15

Leu Ala Ser Ser Asp Thr Phe Pro Val Ile Ala Arg Ser Ser Ala Cys
            20                  25                  30

Arg Ser Leu Phe Gly Pro Val Asp His Glu Glu Leu Gly Arg Glu Leu
        35                  40                  45

Arg Met Arg Leu Ala Glu Leu Asn Ala Glu Asp Gln Asn Arg Trp Asp
    50                  55                  60

Phe Asn Phe Gln Gln Asp Val Pro Leu Arg Gly Pro Gly Arg Leu Gln
65                  70                  75                  80

Trp Met Glu Val Asp Ser Glu Ser Val Pro Ala Phe Tyr Arg Glu Thr
                85                  90                  95

Val Gln Val Gly Arg Cys Arg Leu Gln Leu Gly Pro Arg Pro Pro Pro
            100                 105                 110

Val Ala Val Ala Val Ile Pro Arg Ser Gly Pro Pro Ala Gly Glu Ala
            115                 120                 125

Pro Asp Gly Leu Glu Glu Ala Pro Glu Gln Pro Pro Ser Ala Pro Ala
    130                 135                 140

Ser Ala Val Val Ala Asp Ala Thr Pro Pro Ala Thr Pro Ala Pro Ala
145                 150                 155                 160

Ser Asp Leu Thr Ser Asp Pro Ile Pro Glu Val Thr Leu Val Ala Thr
                165                 170                 175

Ser Asp Pro Thr Pro Asp Pro Ile Pro Asp Ala Asn Pro Asp Val Ala
            180                 185                 190

Thr Arg Asp Gly Glu Glu Gln Val Pro Glu Gln Val Ser Glu Gln Gly
    195                 200                 205

Glu Glu Ser Gly Ala Glu Pro Gly Asp Glu Leu Gly Thr Glu Pro Val
    210                 215                 220

Ser Glu Gln Gly Glu Glu Gln Gly Ala Glu Pro Val Glu Glu Lys Asp
225                 230                 235                 240

Glu Glu Pro Glu Glu Glu Gln Gly Ala Glu Pro Val Glu Glu Gln Gly
                245                 250                 255

Ala Glu Pro Val Glu Glu Gln Asn Gly Glu Pro Val Glu Glu Gln Asp
            260                 265                 270

Glu Asn Gln Glu Gln Arg Gly Gln Glu Leu Lys Asp Gln Pro Leu Ser
    275                 280                 285

Gly Ile Pro Gly Arg Pro Ala Pro Gly Thr Ala Ala Asn Ala Asn
    290                 295                 300

Asp Phe Phe Ala Lys Arg Lys Thr Ala Gln Glu Asn Lys Ala Ser
305                 310                 315                 320

Asn Asp Val Pro Pro Gly Cys Pro Ser Pro Asn Val Ala Pro Gly Val
                325                 330                 335

Gly Ala Val Glu Gln Thr Pro Arg Lys Arg Leu Arg
            340                 345
```

(2) INFORMATION FOR SEQ ID NO:14:

(i) SEQUENCE CHARACTERISTICS:
        (A) LENGTH: 1355 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 41..1087

(xi) SEQUENCE DESCRIPTION: SEQ ID NO:14:

```
CCGCAGGAGC CGTCCATCAC CAATCAGCCA GCCTTCGACC ATG GGC ATG TCC GAC          55
                                             Met Gly Met Ser Asp
                                              1               5

GTG TAC CTC CGC AGC AGA ACA GCG ATG GAA CGC TTG GCC TCC AGC GAT         103
Val Tyr Leu Arg Ser Arg Thr Ala Met Glu Arg Leu Ala Ser Ser Asp
             10                  15                  20

ACC TTC CCA GTG ATA GCG CGT AGC AGC GCC TGC CGC AGC CTC TTC GGG         151
Thr Phe Pro Val Ile Ala Arg Ser Ser Ala Cys Arg Ser Leu Phe Gly
                 25                  30                  35

CCT GTA GAC CAC GAG GAG CTG GGC CGC GAG CTG CGG ATG CGC CTG GCC         199
Pro Val Asp His Glu Glu Leu Gly Arg Glu Leu Arg Met Arg Leu Ala
             40                  45                  50

GAG CTG AAC GCC GAG GAC CAG AAC CGC TGG GAC TTC AAC TTC CAG CAG         247
Glu Leu Asn Ala Glu Asp Gln Asn Arg Trp Asp Phe Asn Phe Gln Gln
 55                  60                  65

GAT GTG CCT CTT CGA GGC CCT GGT CGT CTG CAG TGG ATG GAG GTG GAC         295
Asp Val Pro Leu Arg Gly Pro Gly Arg Leu Gln Trp Met Glu Val Asp
 70                  75                  80                  85

AGC GAG TCT GTG CCC GCC TTC TAC CGC GAG ACG GTG CAG GTG GGG CGC         343
Ser Glu Ser Val Pro Ala Phe Tyr Arg Glu Thr Val Gln Val Gly Arg
                 90                  95                 100

TGT CGC CTG CAG CTG GGG CCC CGG CCA CCC CCG GTG GCC GTG GCT GTC         391
Cys Arg Leu Gln Leu Gly Pro Arg Pro Pro Pro Val Ala Val Ala Val
            105                 110                 115

ATC CCG CGT TCT GGG CCG CCG GCT GGC GAG GCC CCC GAC GGC CTA GAG         439
Ile Pro Arg Ser Gly Pro Pro Ala Gly Glu Ala Pro Asp Gly Leu Glu
            120                 125                 130

GAG GCG CCT GAG CAG CCG CCC AGC GCC CCA GCC TCG GCC GTG GTC GCG         487
Glu Ala Pro Glu Gln Pro Pro Ser Ala Pro Ala Ser Ala Val Val Ala
            135                 140                 145

GAC GCC ACC CCA CCC GCG ACC CCG GCC CCG GCT TCA GAT CTG ACC TCA         535
Asp Ala Thr Pro Pro Ala Thr Pro Ala Pro Ala Ser Asp Leu Thr Ser
150                 155                 160                 165

GAC CCA ATT CCG GAG GTG ACC CTG GTC GCG ACC TCC GAC CCG ACT CCG         583
Asp Pro Ile Pro Glu Val Thr Leu Val Ala Thr Ser Asp Pro Thr Pro
                170                 175                 180

GAC CCG ATC CCG GAC GCG AAC CCG GAC GTG GCG ACT CGG GAC GGC GAG         631
Asp Pro Ile Pro Asp Ala Asn Pro Asp Val Ala Thr Arg Asp Gly Glu
                185                 190                 195

GAA CAG GTC CCT GAG CAG GTC TCT GAG CAG GGC GAG GAG TCG GGT GCT         679
Glu Gln Val Pro Glu Gln Val Ser Glu Gln Gly Glu Glu Ser Gly Ala
            200                 205                 210

GAG CCG GGT GAT GAG CTG GGA ACT GAG CCG GTC TCT GAG CAG GGC GAG         727
Glu Pro Gly Asp Glu Leu Gly Thr Glu Pro Val Ser Glu Gln Gly Glu
            215                 220                 225

GAG CAG GGC GCA GAG CCG GTC GAG GAG AAG GAC GAG GAG CCG GAG GAG         775
Glu Gln Gly Ala Glu Pro Val Glu Glu Lys Asp Glu Glu Pro Glu Glu
230                 235                 240                 245

GAG CAG GGC GCG GAG CCG GTC GAG GAG CAG GGT GCG GAG CCG GTC GAG         823
Glu Gln Gly Ala Glu Pro Val Glu Glu Gln Gly Ala Glu Pro Val Glu
                250                 255                 260

GAG CAG AAT GGG GAG CCG GTC GAG GAG CAG GAC GAG AAT CAA GAG CAG         871
```

```
                                                                             -continued Glu Gln Asn Gly Glu Pro Val Glu Glu Gln Asp Glu Asn Gln Glu Gln
            265                 270                 275

CGC GGC CAG GAG CTG AAG GAC CAG CCT CTC TCG GGG ATT CCA GGA CGT              919
Arg Gly Gln Glu Leu Lys Asp Gln Pro Leu Ser Gly Ile Pro Gly Arg
        280                 285                 290

CCT GCA CCC GGG ACT GCT GCG GCC AAT GCG AAC GAC TTC TTC GCC AAG              967
Pro Ala Pro Gly Thr Ala Ala Ala Asn Ala Asn Asp Phe Phe Ala Lys
295                 300                 305

CGC AAG AGA ACT GCG CAG GAG AAC AAG GCG TCG AAC GAC GTC CCT CCA              1015
Arg Lys Arg Thr Ala Gln Glu Asn Lys Ala Ser Asn Asp Val Pro Pro
310                 315                 320                 325

GGG TGT CCC TCT CCA AAC GTG GCT CCT GGG GTG GGC GCG GTG GAG CAG              1063
Gly Cys Pro Ser Pro Asn Val Ala Pro Gly Val Gly Ala Val Glu Gln
                330                 335                 340

ACC CCG CGC AAA CGT CTG AGA TGA GTTAGTTTAG AGGCTAACGG CCAGAGAGAA             1117
Thr Pro Arg Lys Arg Leu Arg *
                345

CTTGCTGGGC ATCTGGGCAG CGGACGATGG AAGAACTCTG GGCTTCGGCT GGGACCTTTC            1177

GTTCATGTAG CAGGAACCGG AGATGGTTGC GTAGAGCAGC CCACGGTTTT GTGGAAATCT            1237

GAAAACTGTG CAATGTATTG AGAACACTCT GTACCATGTG CAAGGAGTAC GCTGGTCCCA            1297

AGGTGTAAAG CTTTAAATCA TTTATGTAAA ATGTTTAATC TCTACTCGCT CTCAGTGC             1355

(2) INFORMATION FOR SEQ ID NO:15:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:15:

Met Gly Met Ser Asp Val Tyr Leu Arg Ser Arg Thr Ala Met Glu Arg
 1               5                  10                  15

Leu Ala Ser Ser Asp Thr Phe Pro Val Ile Ala Arg Ser Ser Ala Cys
            20                  25                  30

Arg Ser Leu Phe Gly Pro Val Asp His Glu Glu Leu Gly Arg Glu Leu
        35                  40                  45

Arg Met Arg Leu Ala Glu Leu Asn Ala Glu Asp Gln Asn Arg Trp Asp
    50                  55                  60

Phe Asn Phe Gln Gln Asp Val Pro Leu Arg Gly Pro Gly Arg Leu Gln
65                  70                  75                  80

Trp Met Glu Val Asp Ser Glu Ser Val Pro Ala Phe Tyr Arg Glu Thr
                85                  90                  95

Val Gln Val Gly Arg Cys Arg Leu Gln Leu Gly Pro Arg Pro Pro Pro
            100                 105                 110

Val Ala Val Ala Val Ile Pro Arg Ser Gly Pro Pro Ala Gly Glu Ala
        115                 120                 125

Pro Asp Gly Leu Glu Glu Ala Pro Glu Gln Pro Pro Ser Ala Pro Ala
    130                 135                 140

Ser Ala Val Val Ala Asp Ala Thr Pro Pro Ala Thr Pro Ala Pro Ala
145                 150                 155                 160

Ser Asp Leu Thr Ser Asp Pro Ile Pro Glu Val Thr Leu Val Ala Thr
                165                 170                 175

Ser Asp Pro Thr Pro Asp Pro Ile Pro Asp Ala Asn Pro Asp Val Ala
            180                 185                 190
```

```
-continued

Thr Arg Asp Gly Glu Glu Gln Val Pro Glu Gln Val Ser Glu Gln Gly
        195                 200                 205

Glu Glu Ser Gly Ala Glu Pro Gly Asp Glu Leu Gly Thr Glu Pro Val
        210                 215                 220

Ser Glu Gln Gly Glu Glu Gln Gly Ala Glu Pro Val Glu Glu Lys Asp
225                 230                 235                 240

Glu Glu Pro Glu Glu Glu Gln Gly Ala Glu Pro Val Glu Glu Gln Gly
                245                 250                 255

Ala Glu Pro Val Glu Glu Gln Asn Gly Glu Pro Val Glu Glu Gln Asp
            260                 265                 270

Glu Asn Gln Glu Gln Arg Gly Gln Glu Leu Lys Asp Gln Pro Leu Ser
        275                 280                 285

Gly Ile Pro Gly Arg Pro Ala Pro Gly Thr Ala Ala Ala Asn Ala Asn
        290                 295                 300

Asp Phe Phe Ala Lys Arg Lys Arg Thr Ala Gln Glu Asn Lys Ala Ser
305                 310                 315                 320

Asn Asp Val Pro Pro Gly Cys Pro Ser Pro Asn Val Ala Pro Gly Val
                325                 330                 335

Gly Ala Val Glu Gln Thr Pro Arg Lys Arg Leu Arg
        340                 345
```